(12) United States Patent
Fischell et al.

(10) Patent No.: US 12,268,417 B2
(45) Date of Patent: Apr. 8, 2025

(54) ENHANCED GUIDE EXTENSION SYSTEM FOR THE EFFICIENT DELIVERY OF LEADS

(71) Applicant: VANTIS VASCULAR, INC., Kalamazoo, MI (US)

(72) Inventors: Tim A. Fischell, Kalamazoo, MI (US); Frank S. Saltiel, Willowbrook, IL (US); Xiaoke Liu, Portage, MI (US); Jeffrey D. Payne, Temecula, CA (US)

(73) Assignee: VANTIS VASCULAR, INC., Kalamazoo, MI (US)

( * ) Notice: Subject to any disclaimer, the term of this patent is extended or adjusted under 35 U.S.C. 154(b) by 0 days.

(21) Appl. No.: 18/648,932

(22) Filed: Apr. 29, 2024

(65) Prior Publication Data
US 2024/0268862 A1     Aug. 15, 2024

Related U.S. Application Data

(63) Continuation of application No. 18/411,524, filed on Jan. 12, 2024, now Pat. No. 11,998,236, which is a
(Continued)

(51) Int. Cl.
*A61B 17/34*     (2006.01)
*A61M 25/06*     (2006.01)
(Continued)

(52) U.S. Cl.
CPC ...... *A61B 17/3468* (2013.01); *A61B 17/3462* (2013.01); *A61M 25/0637* (2013.01);
(Continued)

(58) Field of Classification Search
CPC ............ A61M 25/0668; A61M 25/005; A61M 2025/0675; A61M 25/0637; A61B 17/3468; A61B 17/3462
See application file for complete search history.

(56) References Cited

U.S. PATENT DOCUMENTS 3,388,703 A   6/1968  Bowes
3,633,579 A   1/1972  Alley et al.
(Continued)

FOREIGN PATENT DOCUMENTS

JP    H11-347131       12/1999
WO    WO 2019/164592    8/2019
(Continued)

OTHER PUBLICATIONS

U.S. Appl. No. 16/184,706, filed Nov. 8, 2018, Root et al.
(Continued)

*Primary Examiner* — Majid Jamialahmadi
(74) *Attorney, Agent, or Firm* — Knobbe, Martens, Olson & Bear, LLP

(57) ABSTRACT

Intravascular delivery system is designed for a safe and efficient access to secondary and tertiary vascular structures, such as the branches of the coronary sinus, to enhance the delivery and deployment of various catheters, such as, for example, pacemaker electrical leads. The over-the-wire system features a straight, or alternatively shaped, microcatheter distal tip of an inner catheter that seamlessly cooperates with a peel-away reinforced outer catheter. The inner catheter and the peel-away reinforced outer catheter are advanced in their engaged mode of operation towards (or beyond) the target site. Subsequently, the inner and outer catheters are disengaged, and the inner catheter is removed from the outer catheter. A pacemaker lead may be advanced over the wire inside the outer catheter to the target site for deployment. Subsequently, the outer catheter is easily split and may be rapidly removed from the blood vessel.

12 Claims, 18 Drawing Sheets

Related U.S. Application Data continuation of application No. 18/333,368, filed on Jun. 12, 2023, now Pat. No. 11,903,613, which is a continuation of application No. 17/304,786, filed on Jun. 25, 2021, now Pat. No. 11,712,266.

(51) Int. Cl.
*A61N 1/372* (2006.01)
*A61M 39/22* (2006.01)

(52) U.S. Cl.
CPC ......... *A61M 25/0668* (2013.01); *A61N 1/372* (2013.01); *A61M 2039/229* (2013.01)

(56) References Cited

U.S. PATENT DOCUMENTS

| | | | |
|---|---|---|---|
| 5,102,390 | A | 4/1992 | Crittenden et al. |
| 5,234,416 | A | 8/1993 | Macaulay et al. |
| 5,425,723 | A | 6/1995 | Wang |
| 5,704,926 | A | 1/1998 | Sutton |
| 5,769,819 | A | 6/1998 | Schwab et al. |
| 5,813,405 | A | 9/1998 | Motano, Jr. et al. |
| 5,947,925 | A | 9/1999 | Ashiya et al. |
| 6,120,480 | A | 9/2000 | Zhang et al. |
| 6,179,813 | B1 | 1/2001 | Ballow et al. |
| 6,585,747 | B1 | 7/2003 | Limon et al. |
| 6,648,854 | B1 | 11/2003 | Patterson et al. |
| 7,993,351 | B2 | 8/2011 | Worley et al. |
| 8,048,032 | B2 | 11/2011 | Root et al. |
| 8,142,413 | B2 | 3/2012 | Root et al. |
| 8,292,850 | B2 | 10/2012 | Root et al. |
| 8,361,057 | B2 | 1/2013 | Tanghoej et al. |
| 8,365,087 | B2 | 1/2013 | Glaser-Seidnitzer et al. |
| 8,652,193 | B2 | 2/2014 | Dorn |
| 8,747,428 | B2 | 6/2014 | Fischell et al. |
| 8,821,485 | B2 | 9/2014 | Herberer |
| RE45,380 | E | 2/2015 | Root et al. |
| 8,996,095 | B2 | 3/2015 | Anderson et al. |
| 8,996,096 | B2 | 3/2015 | Kinsley et al. |
| RE45,760 | E | 10/2015 | Root et al. |
| RE45,776 | E | 10/2015 | Root et al. |
| RE46,116 | E | 8/2016 | Root et al. |
| 9,681,882 | B2 | 6/2017 | Garrison et al. |
| 9,687,634 | B2 | 6/2017 | Grovender et al. |
| 9,764,118 | B2 | 9/2017 | Anderson et al. |
| RE47,379 | E | 5/2019 | Root et al. |
| 10,449,339 | B2 | 10/2019 | Wilson et al. |
| 10,786,655 | B2 | 9/2020 | Lenker |
| 11,020,133 | B2 | 6/2021 | Wilson et al. |
| 11,065,019 | B1 | 7/2021 | Chou et al. |
| 11,224,450 | B2 | 1/2022 | Chou et al. |
| 11,399,852 | B2 | 8/2022 | Wilson et al. |
| 11,491,313 | B2 | 11/2022 | Fischell et al. |
| 11,576,691 | B2 | 2/2023 | Chou et al. |
| 11,642,500 | B2 | 5/2023 | Fischell et al. |
| 11,712,266 | B2 | 8/2023 | Fischell et al. |
| 11,903,613 | B2 | 2/2024 | Fischell et al. |
| 11,998,236 | B2 | 6/2024 | Fischell et al. |
| 2002/0087076 | A1 | 7/2002 | Meguro et al. |
| 2002/0183826 | A1 | 12/2002 | Dorn et al. |
| 2003/0097094 | A1 | 5/2003 | Ouriel et al. |
| 2003/0105451 | A1 | 6/2003 | Westlund et al. |
| 2003/0153925 | A1 | 8/2003 | Breskot et al. |
| 2004/0098020 | A1* | 5/2004 | Nardeo ........... A61M 29/00 606/194 |
| 2005/0182387 | A1 | 8/2005 | Webler |
| 2005/0273074 | A1 | 12/2005 | Lewis |
| 2006/0033334 | A1* | 2/2006 | Weber ............ F16L 47/04 285/390 |
| 2008/0183128 | A1 | 7/2008 | Morriss et al. |
| 2008/0281228 | A1 | 11/2008 | Parodi et al. |
| 2009/0018525 | A1 | 1/2009 | Waite et al. |
| 2009/0082800 | A1 | 3/2009 | Janardhan |
| 2009/0156953 | A1 | 6/2009 | Wondka et al. |
| 2010/0082000 | A1 | 4/2010 | Honeck et al. |
| 2010/0305475 | A1 | 12/2010 | Hinchliffe et al. |
| 2011/0054503 | A1 | 3/2011 | Rizk et al. |
| 2011/0112567 | A1 | 5/2011 | Lenker et al. |
| 2011/0301502 | A1 | 12/2011 | Gill |
| 2012/0065590 | A1 | 3/2012 | Bierman et al. |
| 2012/0078096 | A1 | 3/2012 | Krolik et al. |
| 2013/0116701 | A1 | 5/2013 | Wang et al. |
| 2013/0237962 | A1 | 9/2013 | Kawai |
| 2014/0012281 | A1 | 1/2014 | Wang et al. |
| 2014/0018773 | A1 | 1/2014 | Wang et al. |
| 2014/0058251 | A1 | 2/2014 | Stigall et al. |
| 2014/0194918 | A1 | 7/2014 | Tegels |
| 2014/0236088 | A1 | 8/2014 | Al-Rashdan et al. |
| 2014/0276618 | A1 | 9/2014 | Di Caprio et al. |
| 2015/0005801 | A1 | 1/2015 | Marquis et al. |
| 2015/0151090 | A1 | 6/2015 | Sutton et al. |
| 2015/0173782 | A1 | 6/2015 | Garrison et al. |
| 2015/0265806 | A1 | 9/2015 | Kawaguchi |
| 2016/0121080 | A1 | 5/2016 | Cottone |
| 2016/0144155 | A1 | 5/2016 | Simpson et al. |
| 2016/0249942 | A1 | 9/2016 | Olson |
| 2016/0346506 | A1 | 12/2016 | Jackson et al. |
| 2017/0028170 | A1 | 2/2017 | Ho |
| 2018/0008801 | A1 | 1/2018 | Solar et al. |
| 2018/0126121 | A1 | 5/2018 | Mauch |
| 2018/0193042 | A1 | 7/2018 | Wilson et al. |
| 2018/0344493 | A1 | 12/2018 | Epstein |
| 2019/0015631 | A1 | 1/2019 | Comerota et al. |
| 2019/0255297 | A1 | 8/2019 | Fischell et al. |
| 2019/0255299 | A1 | 8/2019 | Fischell et al. |
| 2020/0179661 | A1 | 6/2020 | Fischell et al. |
| 2021/0212707 | A1 | 7/2021 | Chou et al. |
| 2021/0259718 | A1 | 8/2021 | Wilson et al. |
| 2021/0338256 | A1 | 11/2021 | Chou et al. |
| 2022/0047285 | A1 | 2/2022 | Chou et al. |
| 2022/0175401 | A1 | 6/2022 | Wilson et al. |
| 2022/0313292 | A1 | 10/2022 | Wilson et al. |
| 2022/0338888 | A1 | 10/2022 | Chou et al. |
| 2022/0370761 | A1 | 11/2022 | Chou et al. |
| 2022/0409239 | A1 | 12/2022 | Fischell et al. |
| 2023/0122087 | A1 | 4/2023 | Fischell et al. |
| 2023/0293861 | A1 | 9/2023 | Fischell et al. |
| 2023/0404620 | A1 | 12/2023 | Fischell et al. |
| 2024/0123187 | A1 | 4/2024 | Fischell et al. |
| 2024/0138877 | A1 | 5/2024 | Fischell et al. |

FOREIGN PATENT DOCUMENTS

| | | |
|---|---|---|
| WO | WO 2021/167653 | 8/2021 |
| WO | WO 2022/271999 | 12/2022 |
| WO | WO 2024/081328 | 4/2024 |

OTHER PUBLICATIONS

U.S. Appl. No. 16/220,925, filed Nov. 12, 2018, Root et al.
U.S. Appl. No. 16/220,951, filed Dec. 14, 2018, Root et al.
U.S. Appl. No. 16/220,975, filed Dec. 14, 2018, Root et al.
U.S. Appl. No. 16/220,996, filed Dec. 14, 2018, Root et al.
Biometrics, "What are Micro-Catheters?", Sep. 15, 2015.
Extended European Search Report for EP Application No. 20919805.0, dated Feb. 16, 2024; 9 pages.
International Search Report and written Opinion of International Searching Authority (US) Regarding Corresponding Application PCT/US2019/012678, Dated Mar. 25, 2019.
International Search Report and Written Opinion of PCT Application No. PCT/US2020/057064, dated Jan. 25, 2021; 26 pages.
International Search Report and Written Opinion of PCT Application No. PCT/US2022/034800, dated Sep. 23, 2022; 15 pages.
International Search Report and Written Opinion of PCT Application No. PCT/US2023/034964, dated Jan. 23, 2024; 12 pages.

* cited by examiner

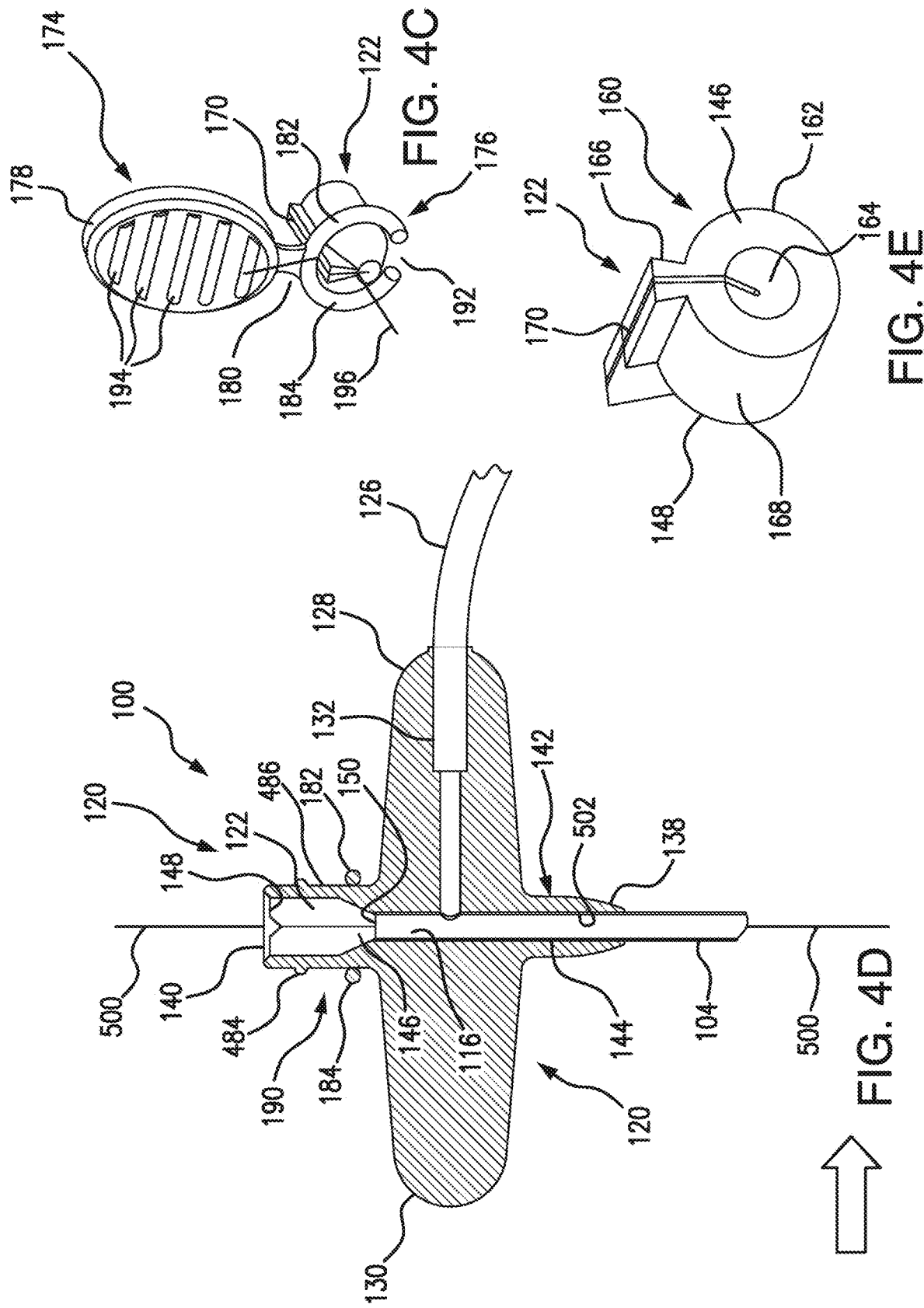

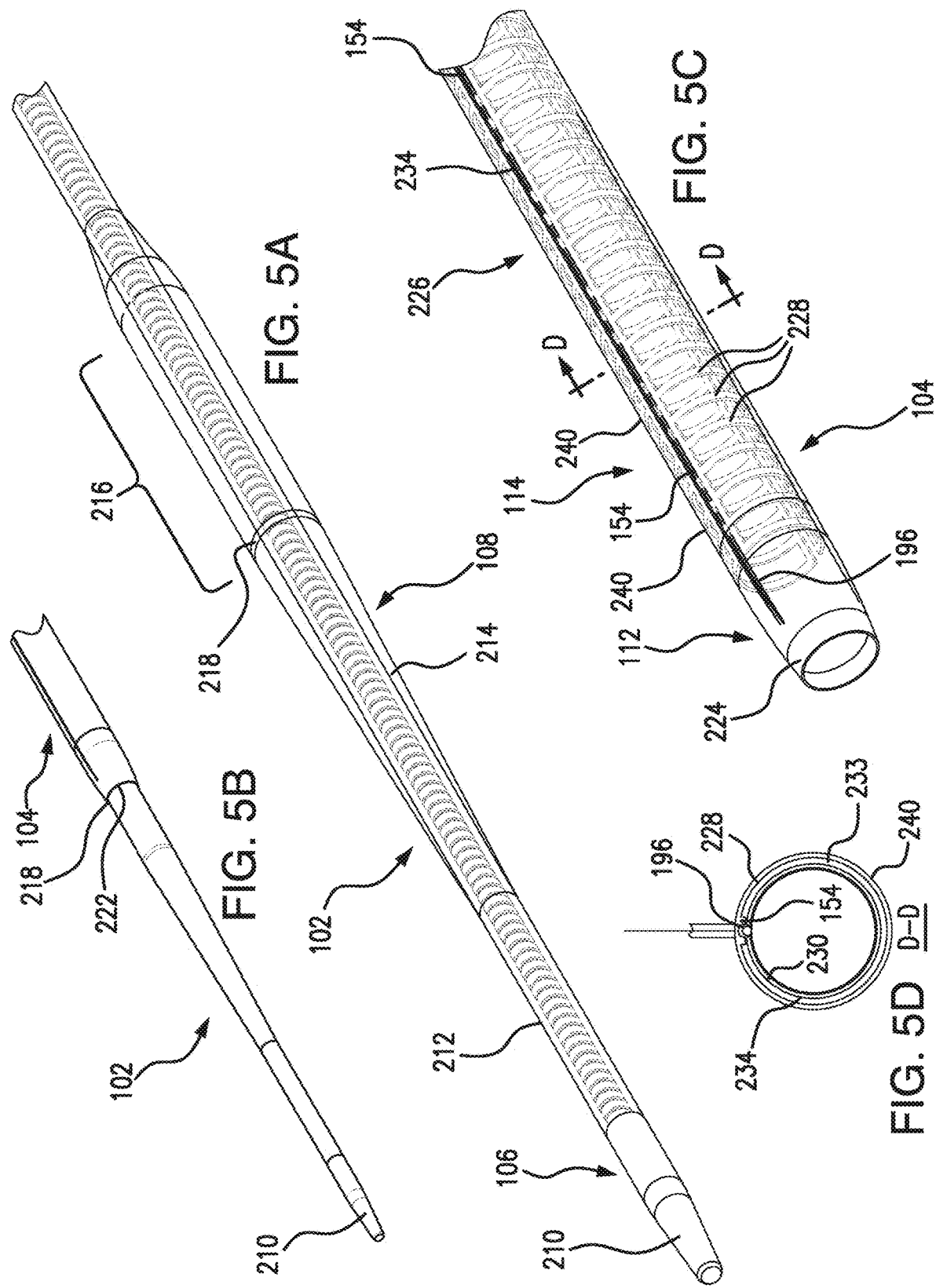

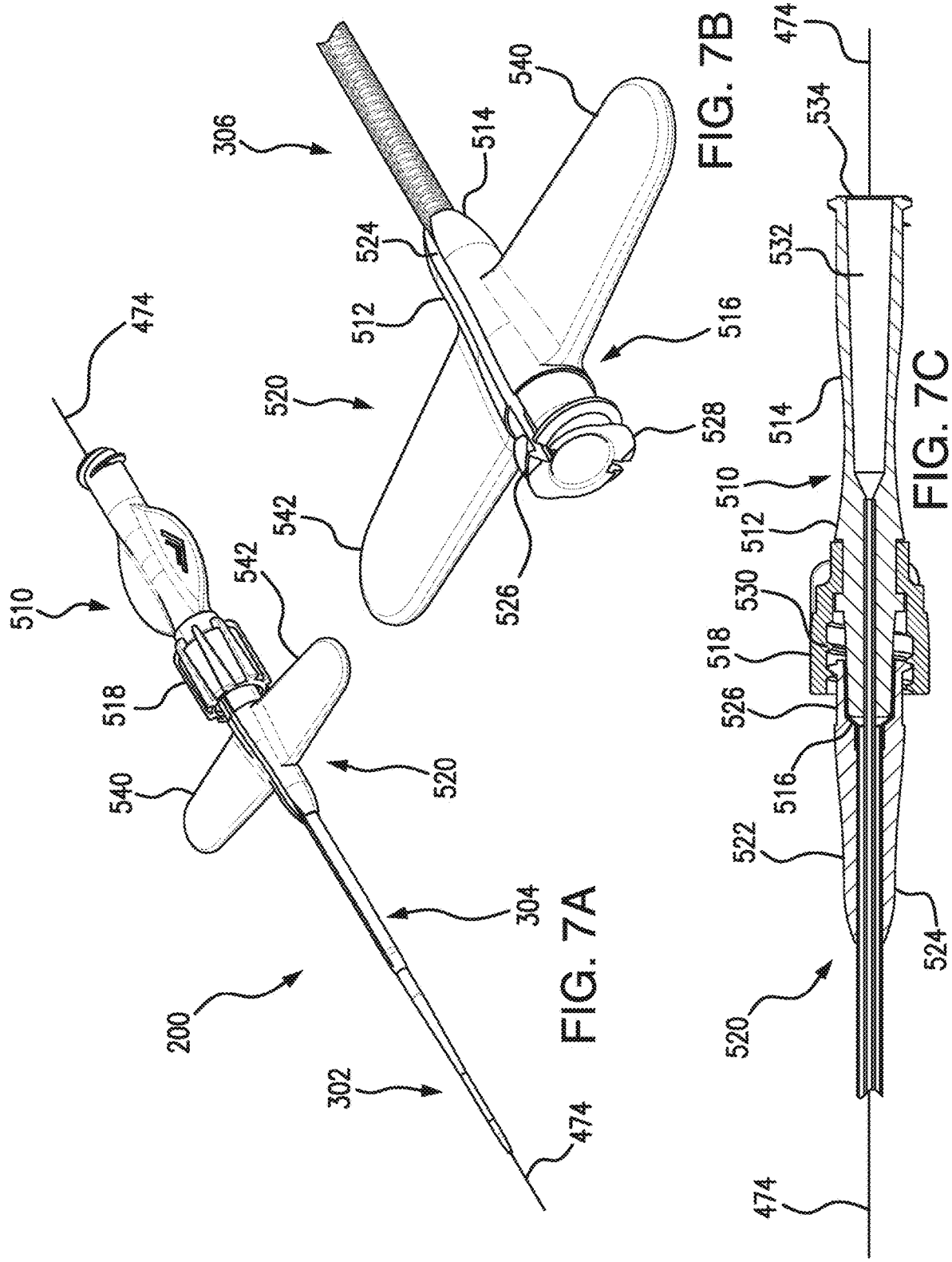

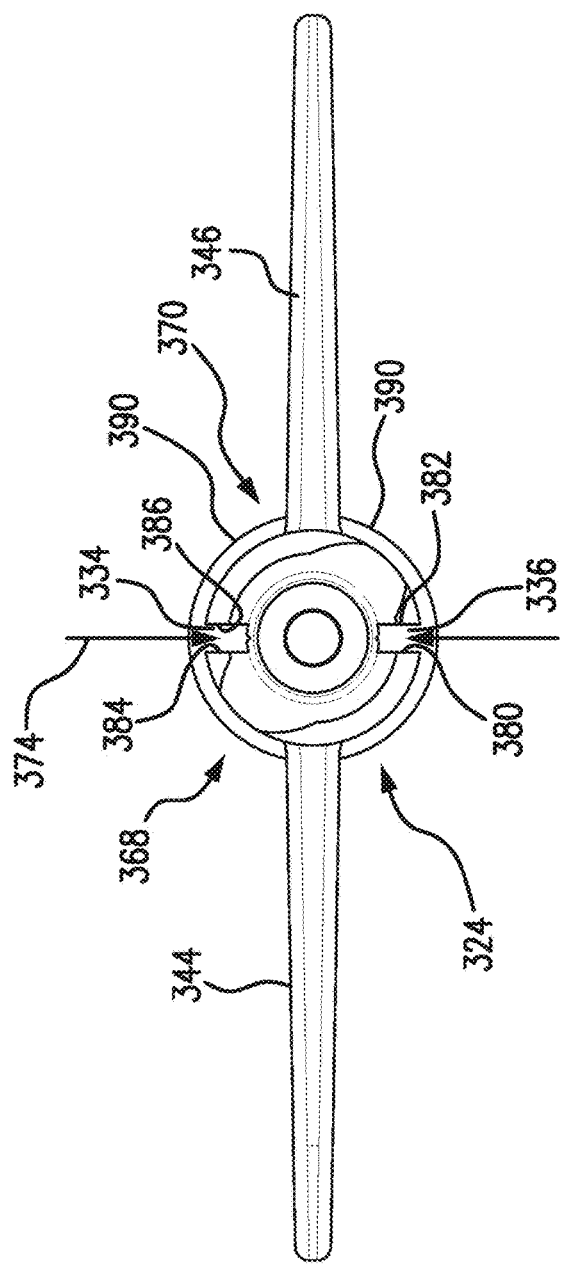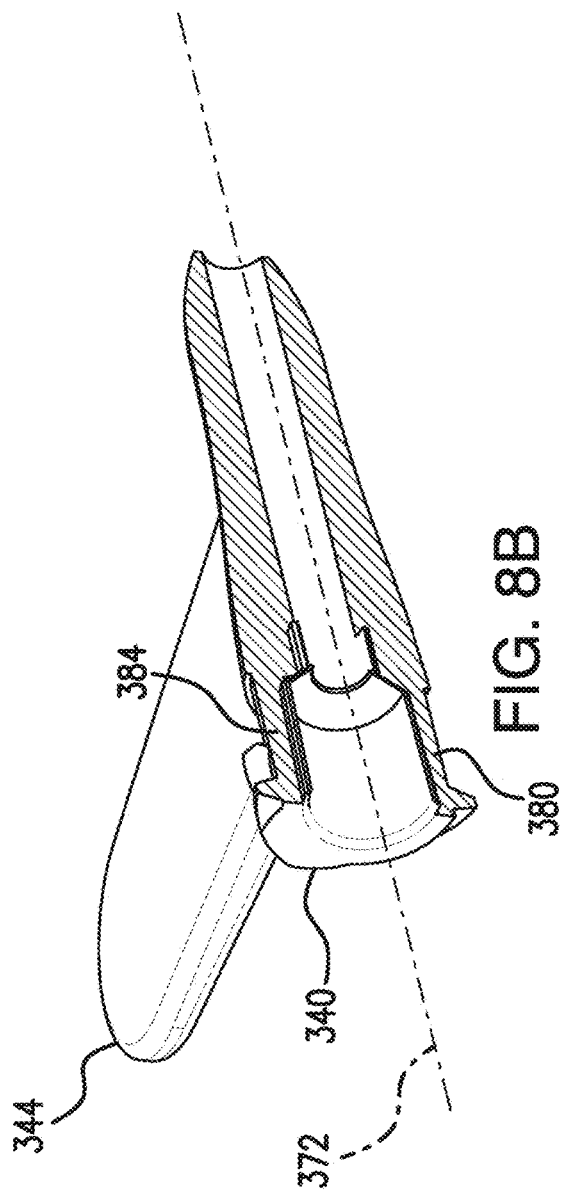

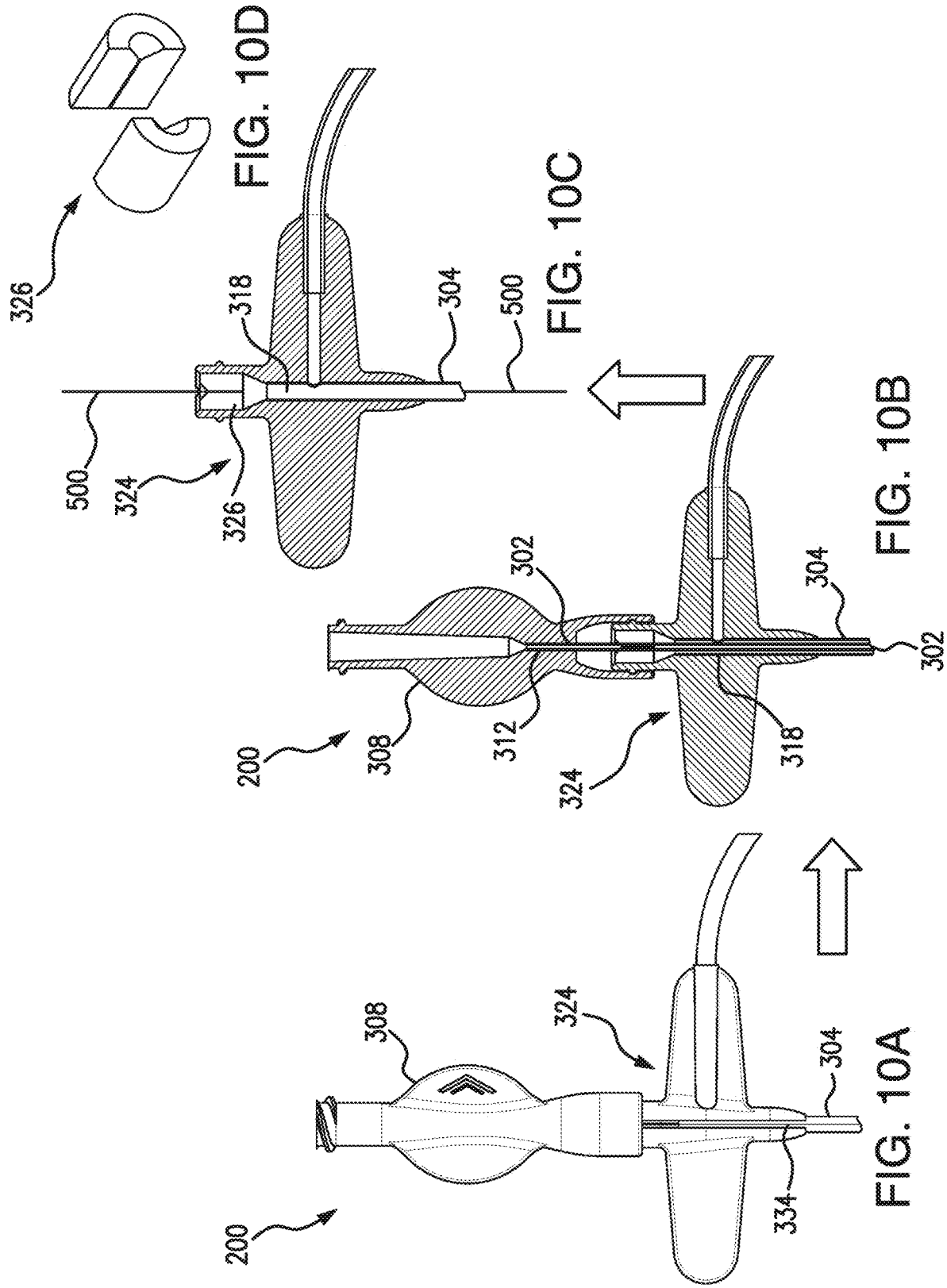

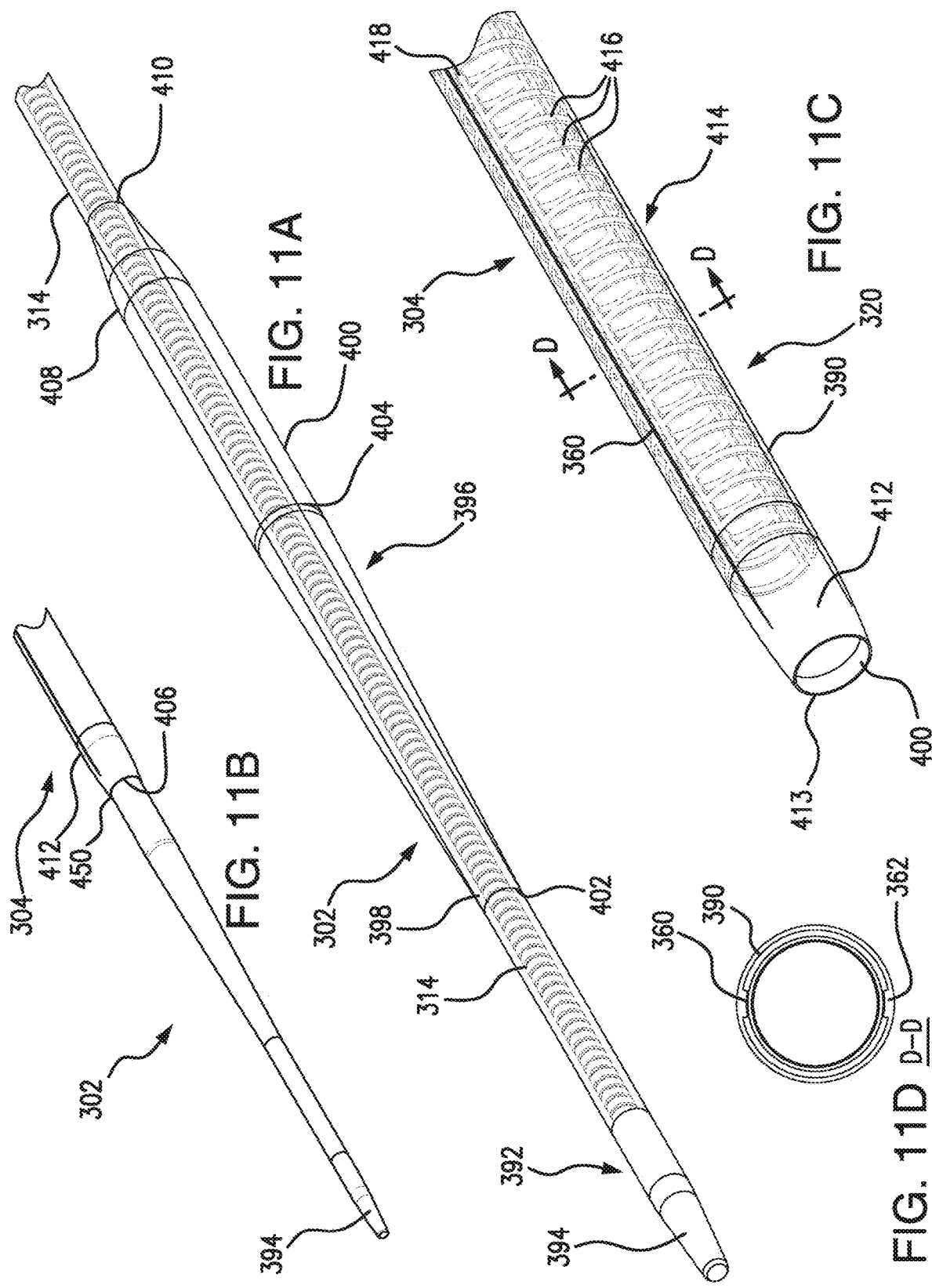

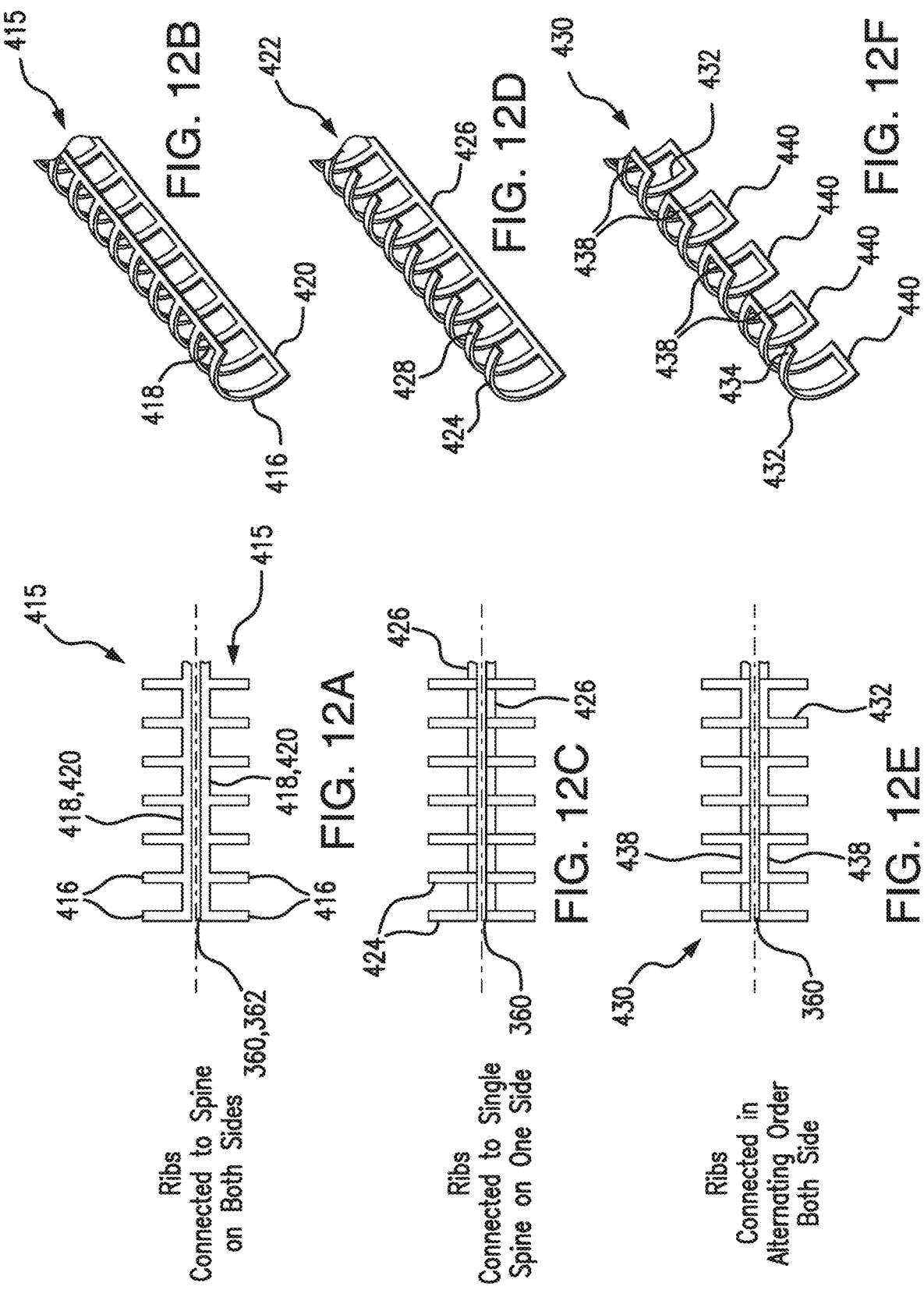

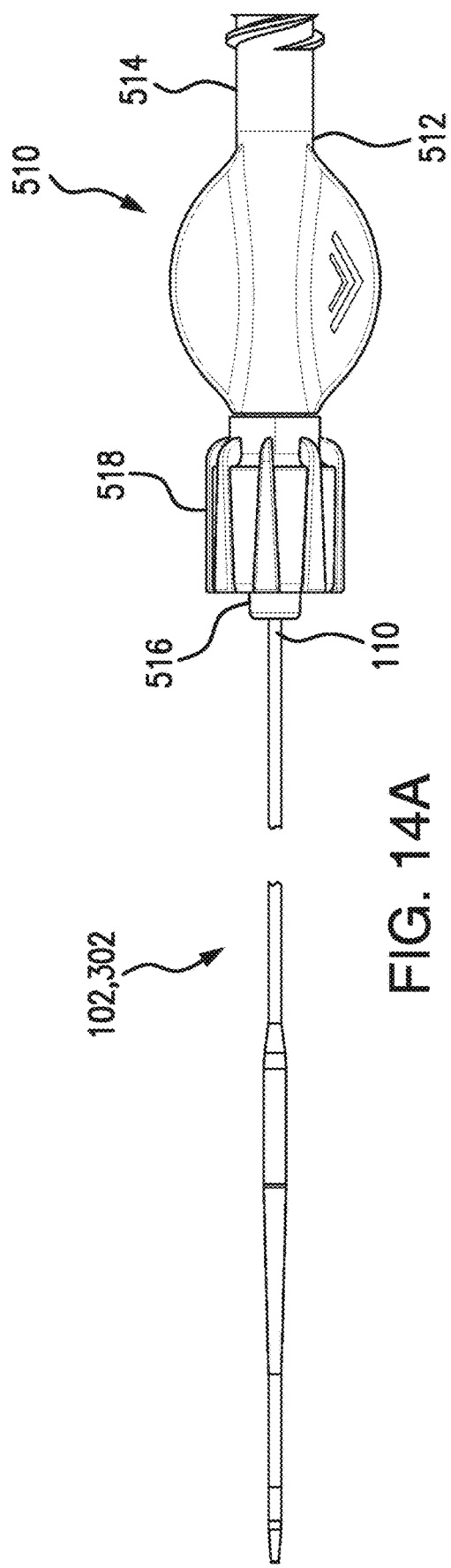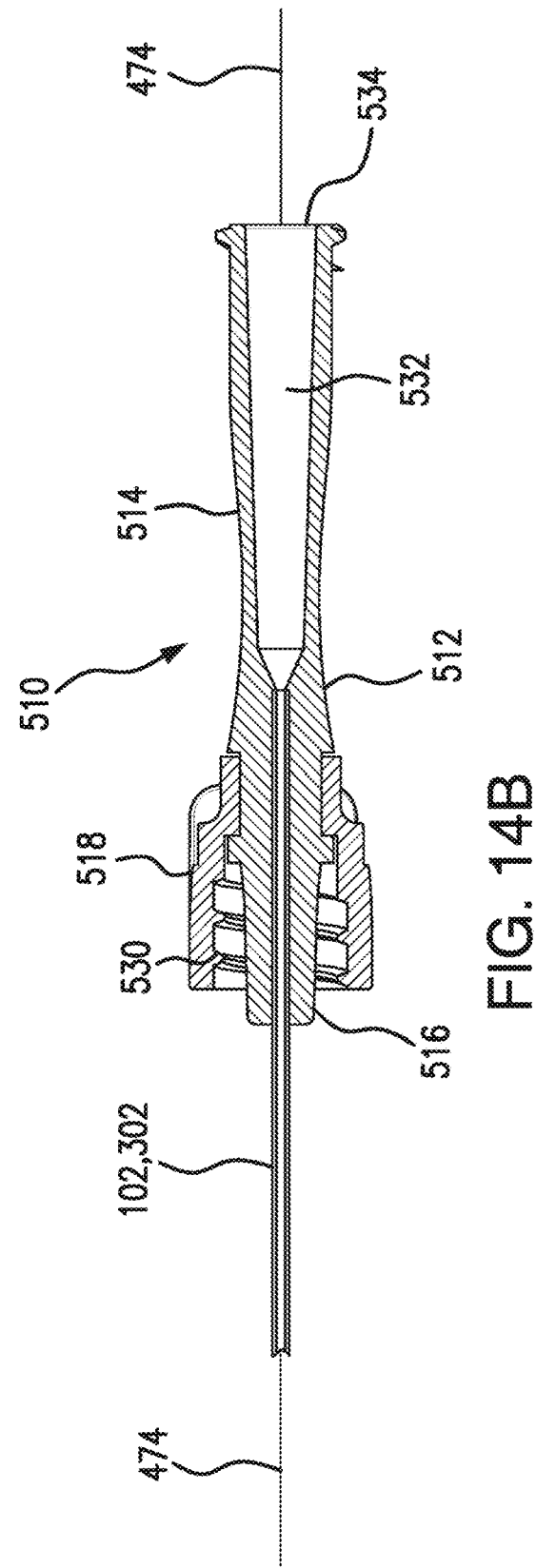
FIG. 14A
FIG. 14B

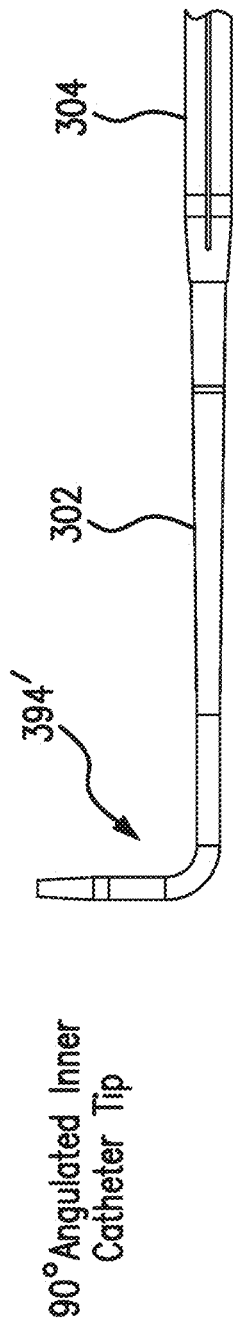
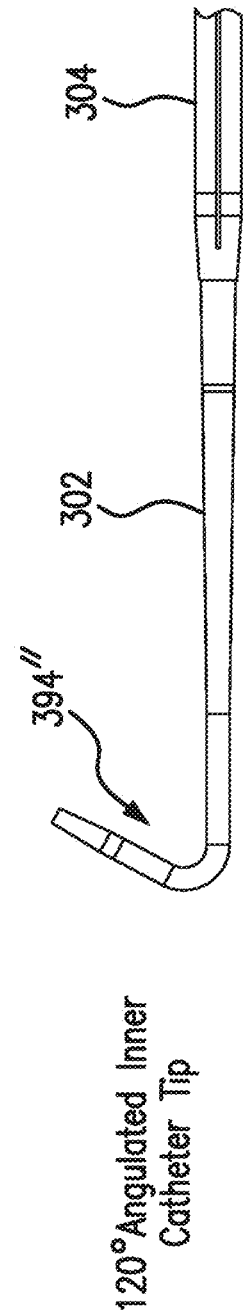
FIG. 15A  90° Angulated Inner Catheter Tip
FIG. 15B  120° Angulated Inner Catheter Tip To FIG.16E

ENHANCED GUIDE EXTENSION SYSTEM FOR THE EFFICIENT DELIVERY OF LEADS

CROSS-REFERENCE TO RELATED APPLICATIONS

This application is a continuation of U.S. patent application Ser. No. 18/411,524, filed Jan. 12, 2024, which is a continuation of U.S. patent application Ser. No. 18/333,368, filed Jun. 12, 2023, which is a continuation of U.S. patent application Ser. No. 17/304,786, filed Jun. 25, 2021, the entirety of each is hereby incorporated by reference herein.

FIELD OF INVENTION

The present invention is directed to medical devices and particularly, to devices designed for atraumatic, fast and efficient delivery and placement of catheters to a target location in various blood vessels in a patient's body for cardiovascular therapy.

The present invention is also directed to an enhanced guide extension system for a safe and simple delivery and access to various blood vessels, including secondary and tertiary vascular structures, such as the branches of the coronary sinus, of the patient's body.

The present invention is further directed to a guide extension system for an enhanced delivery of catheters, such as, for example, pacemaker electrical leads, to a target vein segment in a complicated anatomy of vascular structure for various therapeutic procedures, including cardiac resynchronization therapy, and other cardio-management methodologies for patients with heart failure problems.

Furthermore, the present invention is directed to an enhanced over-the-wire guide extension system having an inner catheter that is seamlessly fit in a peel-away (split-table), outer catheter (sheath) that is capable of the simple, quick and safe delivery of a pacemaker lead (or other therapeutic catheter) to a distal location around tortuosity in the cardiac vasculature, such as in a branch of the coronary vein.

The subject invention is further directed to an enhanced guide extension system configured with inner and outer coupled catheters for a joint advancement within a blood vessel in the patient's body to a target location, where the inner catheter is formed with a distal micro-catheter tip which may have various configurations (for example, straight or angularly bent) for improved ease of accessing vessels with reduced trauma to the patient when advanced through the cardiac vasculature.

The present invention in particular is directed to an efficient and safe delivery of pacemaker leads to the heart of a patient, where the inner and outer catheters are jointly delivered over the guide wire to a target location, with subsequent removal of the flexible, tapered, inner catheter from within the outer catheter where the outer catheter is split and peeled away from a pacemaker lead, and is easily removed from the blood vessel in the least traumatic and simple manner.

BACKGROUND OF THE INVENTION

Cardiac resynchronization therapy has become an important tool for the management of patients with heart failure with a reduced eject fraction in combination with ventricular dysynchrony. In order to accomplish restoration of synchrony, it is necessary to pace the heart simultaneously from both the right and left ventricle resulting in the recruitment of areas of delayed myocardial activation. This therapy typically requires passing of pacing leads (pacemaker leads) through the venous system.

The passage of the pacemaker lead is straightforward for the right ventricle (RV) as the superior vena cava leads directly to the right atrium and subsequently through the tricuspid valve into the right ventricle with the pacemaker lead placed at the apex of that ventricle.

For the left ventricle (LV), the passage of the pacemaker lead is a more challenging procedure. In the LV passage technique, the pacemaker lead is commonly advanced through the coronary sinus (CS) and into an epicardial vein that is located on the epicardial surface of the left ventricle. The CS orifice is located in the posteroseptal region of the right atrium. The coronary sinus runs posteriorly in the atrioventricular groove in between the left atrium and the left ventricle.

The anatomy of the CS is highly variable with a median of 6 branches draining the left ventricle into the CS. The posterolateral veins are typically selected as the site for the pacemaker lead deployment. Once the CS ostium is cannulated with a guiding catheter, a balloon tipped angiography catheter may be advanced into the CS, and subsequently an occlusion venogram is performed to allow selection of possible venous targets.

In an uncomplicated anatomy, the target vein segment can be accessed using a coronary guidewire, followed by the advancement of an over-the-wire lead into the branch vein. However, anatomical challenges are often encountered which impede lead advancement. The anatomical challenges are related to small caliber veins, angulation or tortuosity of venous branches, or stenotic venous branches. Due to these technical challenges, the implantation failure rate for transvenous CS leads may be as high as approximately 10%, and may be even higher considering lead dislodgement rates which may be as high as 6%.

These technical challenges may result in failure to place an LV lead altogether (resulting in an unsuccessful procedure), placing a lead in a suboptimal location, or anchoring the lead in an unstable position. This may not only result in ineffective resynchronization, but may also lead to untoward effects, such as, for example, an unintended stimulation of the phrenic nerve.

In order to address these problems, several specialized devices and techniques have been developed to assist in advancing a pacemaker lead to its intended location. These techniques may, for example, include the use of angulated, pre-shaped micro-catheters of various shapes and configurations, called vein selectors. The vein selectors are advanced distally to engage a branch of interest.

A guidewire can then be directed into the branch of interest. Even with the guidewire in position, in many cases it may not be possible to advance the over-the-wire lead without disengaging (or dislodging) the CS sheath. In order to overcome this problem, a second wire ("buddy") wire may be placed to give additional support. Conversely, a telescoping catheter may be used in conjunction with a pre-shaped catheter and be advanced into the branch. Once the pre-shaped catheter is removed, the pacing lead may be advanced inside the telescoping catheter into the selected branch.

Even more complicated techniques have been developed for particularly challenging anatomy, including, for example, the antidromic snare technique. This technique involves advancing a hydrophilic angioplasty wire in a branch which collateralizes with the target branch, and subsequently advancing the wire through the collateral branch into the target branch. The end of the hydrophilic angioplasty wire is then snared and externalized through the CS sheath. This allows for an extremely stiff "rail" to advance the telescoping guide catheter.

With usage of these various techniques, there has been an improvement in successful and optimal lead placement, with the failed lead placement safe reduced from approximately 8.1% to 1.9%, and the optimal lead positioning rate improved from approximately 75% to 87%.

However, as these maneuvers have become more complicated and aggressive, procedural times can become markedly increased and significant complications may occur. Manipulation of the CS sheath in the distal branches can result in dissection and even perforation of the vessel walls, including resulting pericardial effusions and subsequent tamponade. The catheter manipulation may also affect conduction resulting in a right bundle branch block. Since the majority of the patients undergoing these cardio therapies have underlying left bundle branch block, these complications of the procedure may result in complete heart block or ventricular standstill which is often poorly tolerated especially in patients with reduced ejection fraction.

In addition, prolonged procedure times can result in thrombosis within the CS guide (or telescoping) catheters. This may have the consequence of distal embolization and occlusion of target branches.

Referring to FIGS. 1A-1B, a prior art guide extension system 10 for the delivery of pacemaker leads includes an inner member (also referred to herein as an inner catheter) 12 and an outer catheter (also referred to herein as an outer member) 14. The inner catheter 12 has a distal end 16, a middle section 18, and a proximal section 20. The outer member (catheter) 14 has a distal end 22, a proximal end 24, and a sheath 26 extending between the distal end 22 and the proximal end 24 of the outer catheter 14. An outer catheter hub 28 is located at the proximal end 24 of the outer catheter 14. A proximal hub 30 is positioned at the proximal section 20 of the inner catheter 12.

As shown in FIG. 1A, in the locked position of the inner member 12 and outer member 14, the middle section 18 of the inner catheter 12 is positioned inside the outer catheter 14. In the locked position, the outer catheter hub 28 and the inner catheter hub 30 are snapped and locked together. As shown in FIG. 1B, when the hubs 28 and 30 are disconnected, the hub 30 of the inner catheter 12 is pulled from the outer catheter's hub 28 and the inner catheter 12 can be removed from the outer catheter 14.

The outer catheter hub 28 is a peel-away hub which opens along the groove 38. When during the surgical procedure, the outer catheter 14 is to be released from the peel-away hub 28, a surgeon may displace the wings 40-42 angularly along the arrows 44 and 46 to split the hub 28 along the groove 38. This action opens the outer member peel-away hub 28 and releases the proximal end 24 of the outer catheter 14, thus dislodging the outer catheter 14 from the outer catheter hub 28.

During a surgical procedure, a guidewire is advanced through the vasculature of a patient's body towards the target site, and the system 10 shown in FIGS. 1A-1B is advanced over the guide wire with the inner catheter sliding along the guidewire to the target side. At this stage of the procedure, the system is in its locked mode of operation shown in FIG. 1A.

When a soft distal tip 50 of the inner catheter 12 arrives at the target site, the system may be unlocked, and the outer member 14 may slide along the inner member 12 distally to reach the target site. For this, the system is unlocked, as shown in FIG. 1B, by unsnapping the inner member hub 30 from the outer member hub 28. Subsequently, the inner catheter 12 can be released from the outer catheter 14 so that it can be pulled back as shown in FIG. 1B. Subsequently, a pacemaker lead is inserted into the outer catheter through the proximal end of the hub 28 to advance within the outer catheter 14 beyond the distal tapered soft tip at the distal end of the outer catheter 14 for delivery to the target site.

When the pacemaker lead is delivered to the target site, the outer member hub 28 may be opened along the groove 38 and removed from the vasculature anatomy, as required by the surgical procedure.

Due to the complexities and difficulties, associated with delivering of pacemaker leads, and despite advances in the cardiac-related techniques, there still remains a strong need for an improved pacemaker lead delivery system and technique which provide for an easy, quick, and safe delivery of a pacemaker lead into a complex anatomy of a patient body.

SUMMARY OF THE INVENTION

It is therefore an object of the present invention to provide a guide extension system for a quick, easy and safe delivery with optimal placement of various catheters, including pacemaker leads in the complicated anatomy of a patient's cardiac vasculature.

It is a further object to provide a guide extension system which can overcome anatomical challenges encountered during a pacemaker lead advancement through small caliber veins, angulation or tortuosity of venous branches, or stenotic venous branches.

It is another object of the present invention to provide an over-the-wire guide extension system having an inner catheter with a straight or shaped (hooked) micro-catheter distal tip which is seamlessly fit into a peel-away metal-reinforced outer catheter where the locked inner and outer catheters are jointly advanced in the cardiac vasculature, so that the outer catheter slides over the inner catheter to the target site, and the inner catheter is removed. In this manner the pacemaker lead is delivered to the target site within the outer catheter, and the outer catheter is split and peeled away from the lead for removal from the blood vessel.

In one aspect, the present invention addresses an intravascular delivery system configured for efficient delivery of a therapeutic catheter (for example, a pacemaker lead) to a target site in a blood vessel of interest. The system has a splittable outer member configured to have a flexible substantially cylindrically contoured wall forming an elongated outer delivery sheath defining a sheath lumen. The sheath lumen has a proximal and distal end with an outer member shaft extending between the proximal and distal ends. The outer member shaft is configured with a tapered outer tip at the distal end of the sheath lumen and a tear seam (or plurality of tear seams) extending longitudinally along the cylindrically configured wall of the outer member between the proximal and distal ends of the sheath lumen.

The outer member assumes a closed configuration when the tear seam is intact and has a split apart configuration when the tear seam is opened.

The subject system further includes a seamless inner member having an continuous integral elongated body formed by the inner member wall which defines an internal channel extending along the longitudinal axis of the inner member's elongated body. The inner member is removably received in, and extends internally along the sheath lumen of the outer member in a controllable relationship with the outer delivery sheath. The inner member has a proximal end and a tapered distal tip displaceable along a guide wire beyond the distal end of the outer delivery sheath and an inner member hub secured to the proximal end of the inner member.

The present system is further configured with a splittable outer member hub secured to the proximal end of the sheath lumen of the outer member. The outer member hub has an elongated body configured by a hub wall, and a pair of wing members attached to the elongated body and extending in opposite transverse directions.

The hub wall is formed with a tear groove (or plurality of tear grooves) extending longitudinally along the hub wall of the elongated body of the outer member hub between the proximal and distal ends of the elongated body of the outer member hub. The tear groove of the outer member hub is positioned in substantial alignment with the tear seam of the outer delivery sheath of the outer member.

In operation, the outer member hub may assume either a closed configuration (when the tear groove is closed), and an open configuration (when the tear groove is opened).

The present system is further configured with an interconnection mechanism disposed in an operative coupling with the inner and outer members. The interconnection mechanism is controllably actuated to operate the intravascular delivery system intermittently either in an engaged mode of operation, or in a disengaged mode of operation.

The interconnection mechanism involves the inner member hub and the splittable outer member hub, and operates by the interrelation between the inner member hub and the splittable outer member hub to prevent, or permit displacement of the inner member relative to the outer member.

In the engaged mode of operation, the inner and outer members of the intravascular delivery system are engaged for a controllable common displacement along the guide wire, and in the disengaged mode of operation, the inner and outer members are disengaged for retraction of the inner member from the outer member.

When the inner member is retracted from the outer member, a pacemaker lead may be introduced through the port at the proximal end of the outer member hub's body into the outer member's sheath lumen to the target site for cardio treatment. Subsequent to deployment of the pacemaker lead in the patient's body, the outer member may be peeled-away from the pacemaker lead. In order to accomplish this, the outer member and the outer member hub are split along the tear seam of the outer member and the tear groove of the outer member hub for removal from the blood vessel of interest.

In order to split the outer member and the outer member hub, a surgeon manipulates the wing members on the outer member hub to displace the wing members either angularly or linearly in opposite directions. This action results in the splitting of the outer member and outer member hub along one, two or more tear seam(s)/tear groove(s), respectively.

Preferably, the outer member shaft includes a reinforcement structure extending along a length of the outer member shaft between the proximal and distal ends. The outer member shaft, along with the reinforcement structure, is encapsulated in a flexible encapsulating sheath. A tear wire is encapsulated in the flexible encapsulating sheath in alignment with the tear seam of the outer member shaft.

The present intravascular delivery system further includes a tear-away wire tab member configured with a tab and a C-shaped spring wire member attached to the tab and snapped on the outer member hub at the proximal end of said elongated body of the outer member hub to maintain the elongated body of the outer member hub in the closed configuration.

The tear wire has a proximal end attached to the tear-away wire tab member. In the closed configuration of the outer member and the outer member hub, the tear wire is encapsulated in the outer member's flexible encapsulating sheath and extends within the tear groove of the outer member hub and the tear seam of the outer member, whereas in the open configuration of the outer member and the outer member hub, the tear-away wire tab member is disengaged (lifted) from the outer member hub, resulting in removal of the tear wire from the encapsulated sheath of the outer member and from the tear groove of the outer member hub. This action causes splitting of the outer member hub along the tear groove and ripping of the encapsulating sheath of the outer member along the tear seam, thus resulting in separation (splitting) of the outer member along the tear seam, and a splitting of the outer member hub along the tear groove.

Preferably, the elongated body of the outer member hub includes an internal channel defined by the hub wall and a proximal portion which houses a splittable hemostasis valve therein. The hemostasis valve is configured with a cylindrical body having a valve wall and a longitudinal channel formed by the valve wall in communication with the internal channel of the outer member hub. The valve wall of the cylindrical body of the hemostasis valve is formed with at least one valve groove extending along the valve wall throughout its thickness. The valve groove extends along, and in alignment with the tear groove of the outer member hub. The hemostasis valve may assume a split configuration when the outer member hub is split along its tear groove.

The subject intravascular delivery system further includes a side port stopcock sub-system fluidly coupled to the proximal end of the outer member installed in the outer member hub by way of a side port flexible tubing which may be coupled to at least one of the wing members of the outer member hub. A stopcock, which may be a single-port or multiple-ports valve (or faucet) for regulating/stopping flow of fluid(s) including blood, physiological solutions, etc., or gas(es) through the outer member, may be used dependent upon requirements of the surgical procedure.

The reinforcement structure of the outer member shaft may be configured in numerous alternative forms, for example, with a plurality of C-shaped rings coupled to a spine structure and disposed in mutually spaced apart relationship with each other along the length of the outer shaft member. Each of the C-shaped rings may have an opening aligned with the openings of other C-shaped rings and coinciding with the tear seam of the outer member shaft. The tear wire may be positioned in the aligned openings of the plurality of C-shaped rings.

The elongated body of the inner member may have a reinforced shaft coupled at a distal end to the tapered distal tip, and a tapered element attached to the reinforced shaft in coaxial relationship therewith at a preselected distance from the tapered distal tip. The tapered element of the inner member has a distal end having a distal end diameter, a proximal end having a proximal end diameter, and a landing zone having a landing zone outer diameter between the distal and proximal ends of the tapered element. The distal and proximal end diameters are substantially equal to a diameter of the reinforced shaft of the inner member, while the landing zone outer diameter exceeds the distal end and proximal end diameters and is substantially equal to an internal diameter of the tapered outer tip at the distal end of the sheath lumen of the outer member shaft. In the engaged mode of operation, the landing zone of the tapered element on the inner member is positioned inside the tapered outer tip of the sheath lumen of the outer member shaft lumen of the outer member shaft with a substantially seamless and continuous smooth transition formed therebetween.

In an alternative implementation of the subject intravascular delivery system, the outer member shaft is configured with at least a pair of parallel tear seams spaced apart angularly along a perimeter of the outer member shaft. Similarly, the hub wall of the elongated body of the outer member hub is configured with at least two parallel tear grooves spaced apart angularly along a perimeter of said hub wall and placed in alignment with the at least two tear seams of the outer member shaft.

In this embodiment, the valve wall of the cylindrical body of the splittable hemostasis valve is configured with at least two parallel valve grooves spaced apart angularly along a perimeter of the valve wall of the cylindrical body of the splittable hemostatis valve.

The inner member hub has an inner hub elongated body configuration having a distal portion, a proximal portion, and a central portion between the distal and proximal portions. The distal portion is formed by a quasi-cylindrical wall defining an inner distal cavity of the inner member hub having an internal surface. The proximal and central portions have an internal channel extending longitudinally between a proximal port of the inner member hub and the inner distal cavity of the distal portion of the inner member hub. The proximal end of the inner member extends along the inner distal cavity in the inner member hub and is secured to the inner channel of the inner member hub.

In one implementation, the elongated body of the outer member hub may be configured with a proximal portion having proximal portion wall having an outer surface and defining an internal channel having an internal surface.

In the engaged mode of operation, the proximal portion of the outer member hub is snuggly received in the inner distal cavity of the distal portion of the inner member hub in a contiguous manner.

In order to provide a reliable coupling between the inner member and outer member hubs, an annular groove may be formed which extends annularly at the internal surface of the inner distal cavity of the inner member hub. A matching annular ring protrusion may be formed which extends at the outer surface of the proximal portion wall of the outer member hub in cooperating relationship with the annular groove of the inner member hub. The annular ring protrusion snaps into the annular groove to support coupling between the inner member hub and snaps the outer member hub.

In an alternative implementation of the subject system, the member hub may have an inner member hub elongated body configuration with a distal portion, configured as a male Luer lock, a proximal portion, and a rotating threaded collar having internal threads and positioned externally on the distal portion of the distal portion of the inner member hub's elongated body. The male Luer lock of the inner member hub may be configured with external threads cooperating with a first portion of the internal threads of the rotating threaded collar.

In this implementation, the outer member hub may be configured with a splittable proximal female type Luer lock defining an internal cavity of the outer member hub and having external threads. The male Luer lock of the inner member hub is receiving in the internal cavity of the member hub with the external threads of the female Luer lock of the outer member hub cooperating with a second portion of the internal portion of the rotating threaded collar.

In still another alternative embodiment of the subject intravascular delivery system, the reinforced structure of the outer member shaft may include a plurality of arcuate ribs, each having a first end and a second end, and positioned in a spaced apart relationship with one another along the length of the outer member shaft and connected at least at one of the first and second ends by a spine structure. The first ends of said ribs may be connected by a first spine structure.

In another aspect, the present invention addresses a method for intravascular delivery of a therapeutic catheter which includes the steps of:

(a) establishing an intravascular delivery system including;

a splittable outer member formed by a flexible substantially cylindrically contoured splittable elongated outer delivery sheath defining a sheath lumen having a proximal and distal end, and an outer member hub secured to the proximal end of the splittable outer delivery sheath;

an inner member having an elongated body defining an internal channel extending along the longitudinal axis of the inner member with the inner member being displaceable within the sheath lumen of the outer member, and establishing an interconnection mechanism disposed in an operative coupling with the inner and outer members, and controllably actuated to operate the intravascular delivery system in an engaged or disengaged mode of operation;

(b) controlling the interconnection mechanism to establish the engaged mode of operation;

(c) extending a guide wire along the internal channel of the inner member with a proximal end of the guide wire extending external the proximal end of the inner member, and a distal end of the guide wire extending beyond a distal end of the inner member;

(d) advancing the distal end of the guide wire into a blood vessel of interest towards a target site, and advancing the intravascular delivery system, in the engaged mode of operation, along the guide wire;

(e) controlling the interconnection mechanism to establish the disengaged mode of operation, and sliding the outer member along the inner member to the target site;

(f) withdrawing the inner member from the outer member;

(g) advancing a therapeutic catheter to the target site inside the outer delivery sheath of the outer member which remains within the blood vessel;

(h) splitting the outer delivery sheath along at least one tear seam line; and (i) removing the split outer delivery sheath from the blood vessel upon deployment of the therapeutic catheter has been attained.

These and other objects and advantages of the present invention will be apparent when taken in conjunction with the Patent Drawings and the Detailed Description of the Preferred Embodiment.

BRIEF DESCRIPTION OF THE DRAWINGS

FIGS. 4A-4E are representative of the one-side tear-away implementation of the subject system with FIG. 4A detailing an inner member hub coupled to the outer member one-side tear-away hub, FIG. 4B depicting the cross-section of the system of FIG. 4A, FIG. 4C showing the tear-away wire tab, FIG. 4D depicting a cross-section of the outer member one-side tear-away hub with an integrated splittable hemostasis valve, and FIG. 4E showing a single-piece/split hemostasis valve;

FIGS. 5A-5D detail the distal section of the one-side tear-away implementation of the subject system with FIG. 5A depicting a distal tip of the inner member, FIG. 5B showing a seamless transition between the outer member and the inner member, FIG. 5C showing a reinforced shaft of the outer member, and FIG. 5D depicting a cross-section of the distal section of the reinforced shaft of FIG. 5C, taken along lines D-D;

FIGS. 7A-7B depict the two-sided peel-away implementation of the subject system with a splittable Luer lock, where FIG. 7A shows the assembled system, and FIG. 7B details the splittable Luer lock of the splittable outer member; and FIG. 7C depicts a longitudinal cross-section of the assembled system of FIG. 7A;

FIGS. 8A-8B detail the splittable Luer lock of the two-sided peel-away implementation of the subject system, where FIG. 8A shows the proximal splittable Luer lock's proximal end, and FIG. 8B details a cut-away structure of the proximal splittable Luer lock;

FIGS. 10A-10D show a two-sided peel-away implementation of the subject system with the integrated HVA, wherein FIG. 10A is an external view of the proximal end of the system, FIG. 10B is a cross-section of FIG. 10A with the integrated two-piece/split hemostasis valve, FIG. 10C depicts a cross-section of the proximal end of the outer member hub with the inner member removed, and FIG. 10C depicts detailing a two-piece/split hemostasis valve;

FIGS. 11A-11D are representative of the distal tip of the two-sided peel-away implementation of the subject system, with FIG. 11A showing a distal tip of the inner member, FIG. 11B showing a seamless transition between the outer member and inner member, and FIG. 11C showing a tapered distal tip of the reinforced shaft of the outer member, and FIG. 11D being a cross-section of FIG. 11C taken along Lines D-D;

FIGS. 12A-12F depict reinforced shaft of 12A-12B two-sided peel-away implementation of the subject system, with FIGS. 12A-12B showing a schematics and a perspective view, respectively, of ribs connected to the spine on both sides of the reinforced shaft, FIGS. 12C and 12D illustrating a schematics and a perspective view, respectively, of the ribs connected to a single spine on one side of the reinforced shaft, and FIGS. 12E and 12F showing a schematics and a perspective view, respectively, of another implementation of the ribs connected in alternating order at both sides;

FIGS. 14A-14B show another implementation of the Luer lock lock hub of the inner member of the present system with FIG. 14A detailing a Luer lock lock hub of the inner member, and FIG. 14B showing a cross-section of the inner member's proximal female Luer lock with distal male Luer lock lock with/rotating collar;

FIGS. 15A-15B showing variation of the inner member distal tip, where FIG. 15A is representative of the 90° angulated inner member tip, and FIG. 15B is representative of 120° angulated inner member tip.

DETAILED DESCRIPTION OF THE PREFERRED EMBODIMENT

Figure 1:
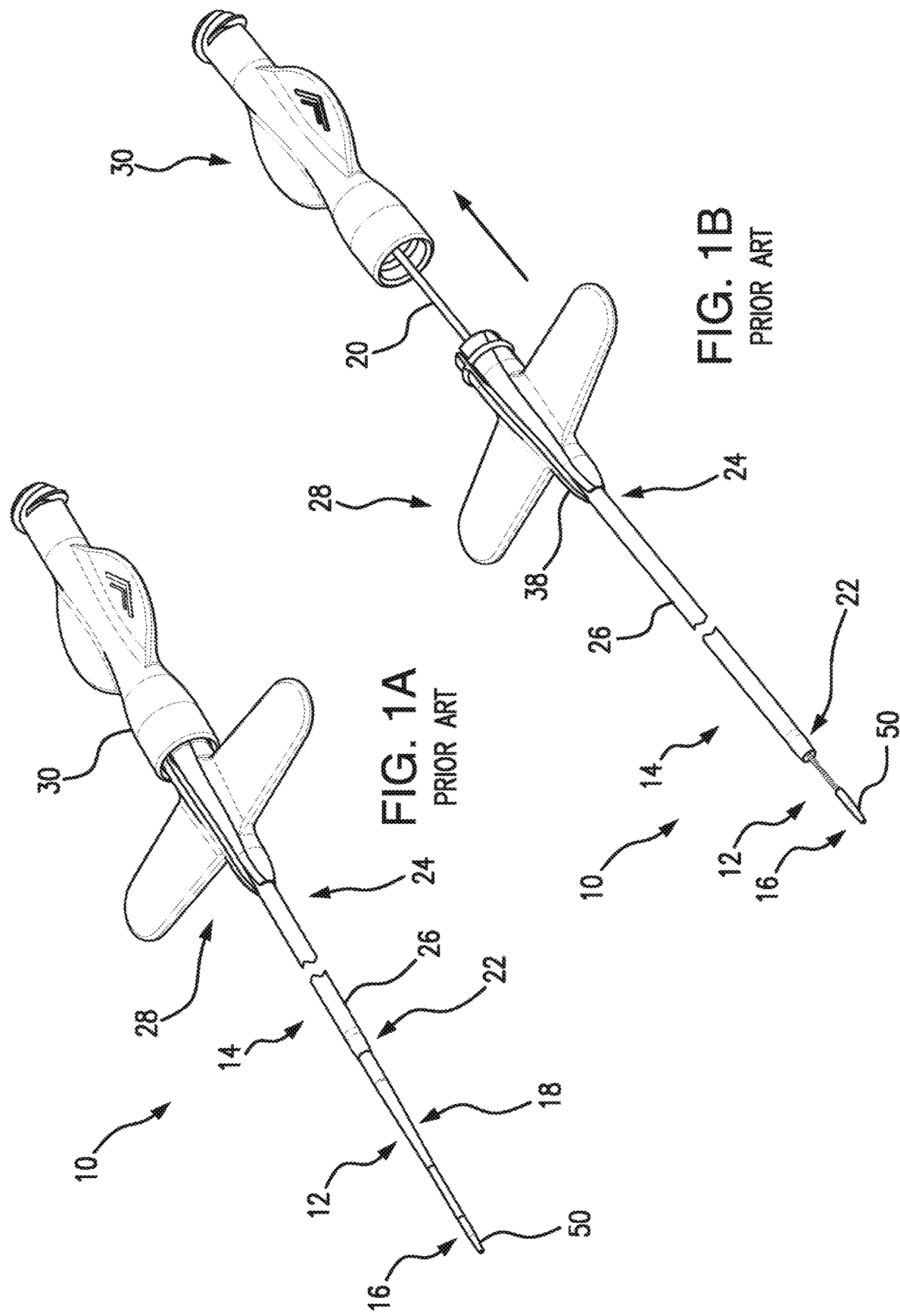
FIGS. 1A-1B are representative of a prior art system in its locked intravascular delivery configuration (FIG. 1A) and its unlocked configuration (FIG. 1B)
Figure 2:
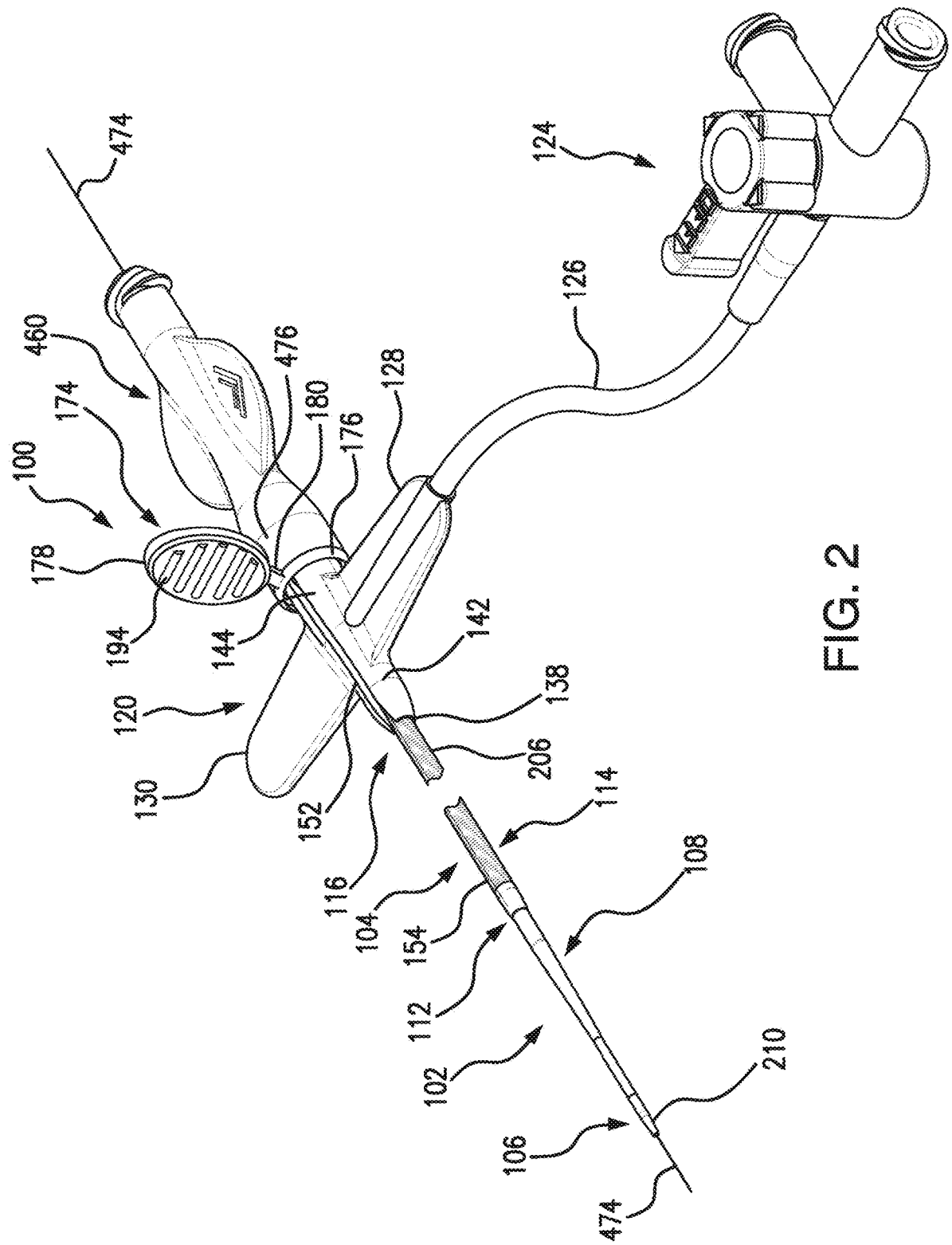
FIG. 2 is representative of the subject intravascular delivery system in the one-side tear-away implementation.

The present system is an improved guide extension delivery system which is designed for efficient delivery of pacemaker leads. Referring to FIGS. 2-5D, the subject system 100 includes an inner member (catheter) 102 and an outer member (catheter) 104. As shown in FIG. 2, the inner catheter 102 is inserted into the outer catheter 104 and may be locked or unlocked from the outer catheter 104.

Shown in FIGS. 2-3, 4A-4E, and 5A-5D, a one-side tear-away implementation of the subject system 100, the inner catheter 102 has a distal section 106, a middle section 108, and a proximal section 110.

The outer catheter 104 includes a distal end 112, another catheter shaft 114, and the proximal end 116 with the outer catheter one-sided tear-away hub 118 removably attached to the proximal end 116 of the outer catheter 104.

As shown in FIGS. 3, 4B-4E, the one-side tear-away hub 120 of the outer catheter 104 has a hemostasis valve 122 integrated therein.

The subject system further includes a side port stopcock 124 which is a valve for regulating/stopping a flow of fluid(s), such as blood, physiological solution(s), etc., to or/from the operational site.

The side port stopcock 124 may be a single- or multi-port structure which is connected to the outer member hub 120 via a flexible tubing 126.

Specifically, the hub 120 is configured with a pair of opposingly extending wing members 128, 130. One of the wing members is formed having an internal conduit 131 extending throughout the length of the wing member 128 or 130, and coupled to an end 132 of the tubing 126. By this mechanism, fluid communication is provided between the surgical site (through the lumen of the outer member 104) and the side port stopcock 124.

The end 132 of the tubing 126 is connected to the proximal end 116 of the outer catheter 104 secured within the hub 120. The site port stopcock 124 has multiple tubing connections for coupling different systems for delivery and removal of fluids during the procedure.

The outer catheter shaft 114 extends between the distal end 112 and the proximal end 116 of the outer catheter 104 and is secured within the internal channel 136 of the outer member 120. The internal channel 136 extends between the distal end 138 and the proximal end 140 of the outer member hub 120. As shown in FIGS. 4A-4D, the proximal end 116 of the outer catheter 104 is secured in the internal channel 136 of the outer member hub 120.

At the proximal end 140 of the outer member hub 120, the hemostasis valve 122 is integrated into the outer member hub 120. The distal end 146 of the hemostasis valve 122 is coupled to the tip 150 of the proximal end 116 of the outer catheter 104. As seen in FIG. 4D, the proximal end 148 of the hemostasis valve 122 is positioned in proximity to the proximal end 140 of the outer member hub 120 which constitutes a port 141 of the outer member hub 120. The outer member hub 120 has a tear groove 152 configured with a quasi-cylindrical body 142 of the hub 120. The groove 152 extends along the walls 144 of the quasi-cylindrical body 142 of the outer member hub 120 between the distal end 146 and the proximal end 148 of the hub body 142.

As seen in FIGS. 2-3 and 5C-5D, the outer catheter shaft 114 of the outer catheter 104 has a groove (or tear seam) 154 extending longitudinally along the length of the outer catheter shaft 114 from the distal end 112 to the proximal end 116.

As shown in FIGS. 4C-4E, the hemostasis valve 122 has a cylindrical body 160 formed by the valve's walls 162. An internal valve channel 164 extends longitudinally along the cylindrical body 160 of the hemostasis valve 122 along its entire length between the distal end 146 and proximal end 148 of the valve 122.

The cylindrical body 160 of the valve 122 is configured with a tab member 166 extending from the outer surface 168 of the walls 162 of the cylindrical body 160 of the valve 122. Referring to FIGS. 4C and 4E, a groove or through channel 170 extends in longitudinal direction of the cylindrical body 160 of the valve 122 through the thickness of the walls 162 and the tab member 166 to provide an open channel. The groove 170 has a length corresponding to the length of the cylindrical body 160 from the distal end 146 to the proximal end 148 of the valve 122 and a depth corresponding to the combined thickness of the walls 162 and the height of the tab member 166.

Figure 4B:
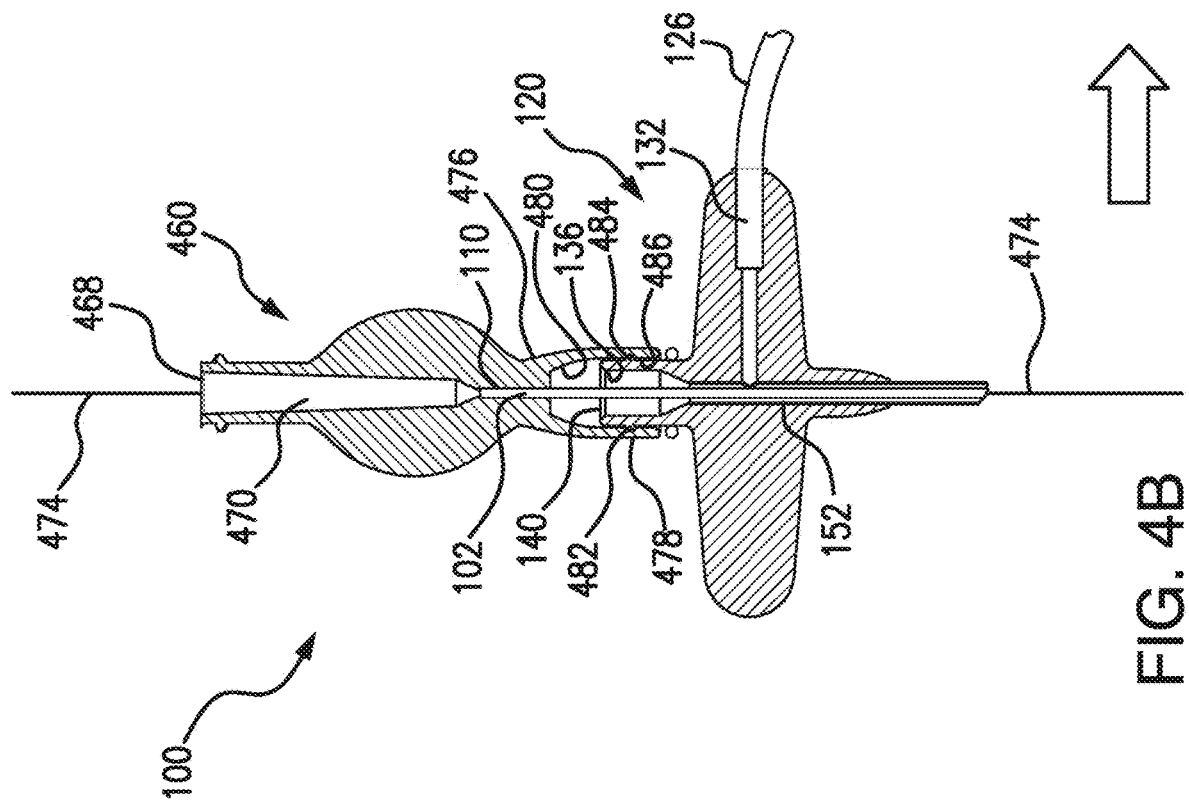

As shown in FIGS. 4B and 4D, the valve 122 is integrated in the outer member hub 120 with the proximal end 148 of the valve 122 in close proximity to the proximal end 140 of the outer member hub 120. The distal end 146 of the valve 122 is coupled to the proximal tip 150 at the proximal end 116 of the outer catheter 104. When integrated within the hub 120, the valve's groove 170 coincides with the hub groove 152 and is aligned with the outer catheter tear seam 154.

Shown in FIGS. 2-3 and 4A-4C and 4D, is a tear away wire tab 174 which is formed with a spring-like member 176 and a tab 178 connected to the spring-like member 176 through the connection element 180. The spring-like member 176 is formed as a C-shaped wire which is resilient and is sufficiently flexible to allow it to be snapped into the hub 120 to maintain the outer member hub 120 in a "closed position".

When the tear away wire tab 174 is positioned on the outer member hub 120, the C-shaped spring-like member 176 is flexibly deformed to permit the proximal portion 190 of the hub 120 to enter the space 192 between the ends of the arms 182 and 184. Once in place, the C-shaped spring-like member 176 resiliently encircles the proximal portion 190 of the hub 120 thus maintaining the hub 120 in its closed position.

The tab 178, which is attached to the spring-like member 176 of the tear away wire tab 174, is shaped with corrugations 194 formed on both sides of the tab 178 to provide an increased frictional grasping impediment for the fingers of a surgeon when the tab 178 is positioned onto the hub 120 or removal therefrom. As shown in FIG. 2, the tear away wire tab 174 is placed on the outer member hub 120 with the spring-like member 176 encircling the proximal portion 190 of the outer member hub 120.

Figure 3:
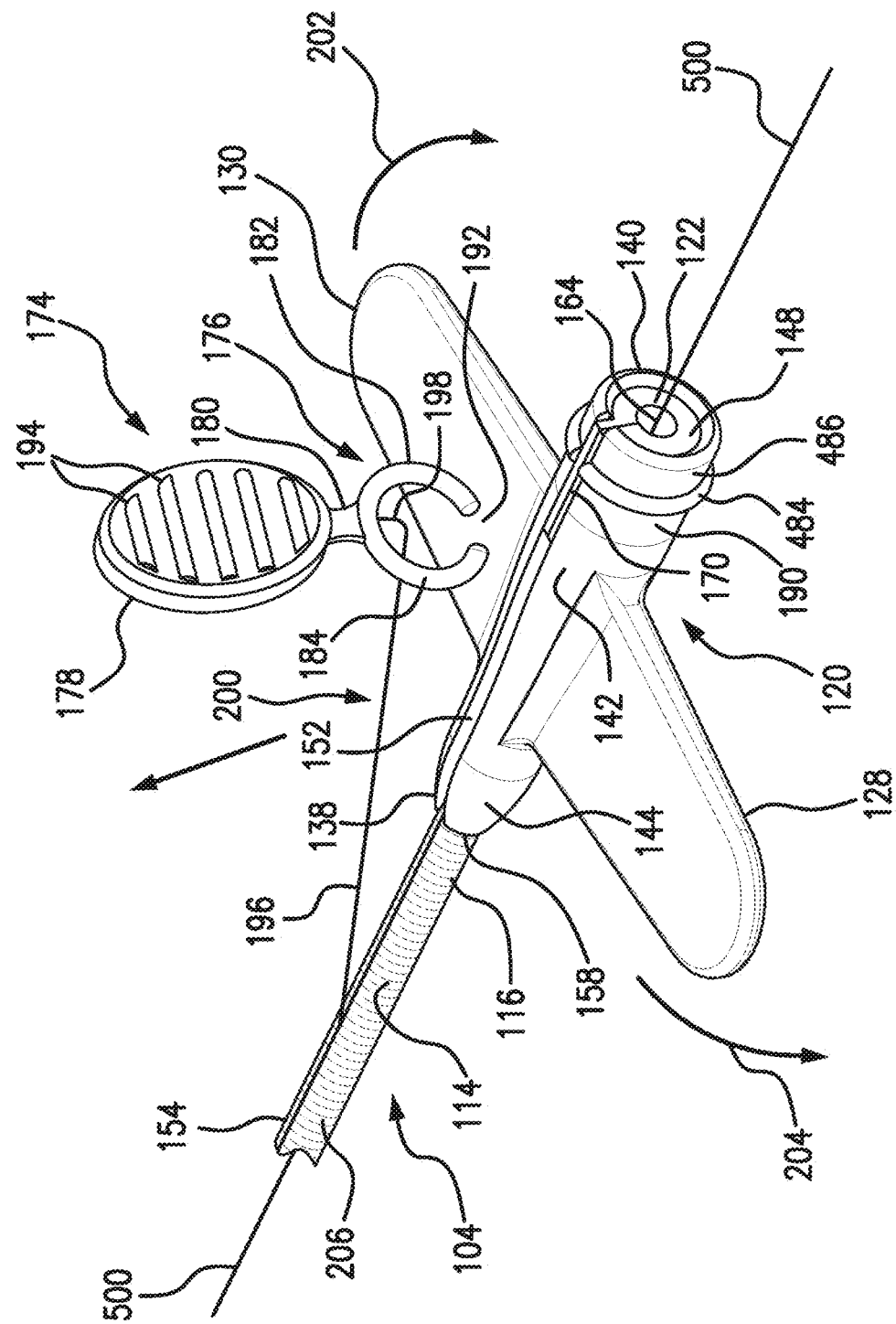
FIG. 3 depicts the proximal section of the tear-away outer member hub and tear-away wire tab in disassembled state.

The tear away wire tab 174 also has a tear cord 196, as seen in FIGS. 3 and 4C which is attached by one end 198 to the tab 178. When the tear away wire tab 174 is secured to the outer member hub 120, the tear cord 196 extends along a distal portion of the valve's groove 170 (shown in FIG. 5C) a portion of the hub groove 152 (between the tip 150 of the outer catheter 104 and the distal end 158 of the outer member hub 120), as well as within the outer catheter groove 154 towards the distal end 112 of the outer catheter 104. When the tear away wire tab 174 is lifted and removed from the hub 120 as shown in FIG. 3, the lifting of the tear away wire tab 174 causes a removal of the cord 196 from the grooves 170, 152, 154 formed in the hemostasis valve 122, outer member hub 120, and the outer member shaft 114 of the outer catheter 104 respectively. With the tear away wire tab 174 removed from the hub 120 and the tear cord 196 removed from the grooves 152, 154 and 170 of the outer member hub 120, outer catheter 104, and the hemostasis valve 122 respectively, the surgeon may press the wings 128 and 130 of the outer member hub 120 in the directions 202 and 204 (FIG. 3) so that the valve 122, hub 120, and the shaft 114 of the outer catheter are split along their respective grooves. In this manner the outer member 104 may be easily removed from within the vascular structure without effecting a pacemaker lead located within the outer catheter.

Subsequent to removal of the tear cord 196 by removing the tear away wire tab 174 from the hub 120, and opening the hub 120, valve 122, and the shaft 114 of the outer catheter 104, the tab member 166 of the valve 122 and the walls 162 of the cylindrical body 160 of the valve 122 are split along the groove 170. In addition, the hub 120 is split along its groove 152, and the walls 206 of the outer shaft 114 of the outer catheter 104 are split along the groove 154. Such arrangement simplifies the surgical procedure and provides a simplified and time saving advantage for the surgeon during the procedure which in most cases is extremely important. This provides for an easy, quick and safe removal of the outer catheter 104 from the vasculature structure when it is pulled out during the surgical procedure.

Referring to FIGS. 5A-5B, the inner catheter 102 has a tapered radiopaque distal soft tip 210 at the distal section 106. A coil and/or braid reinforced shaft 212 extends between the tapered radiopaque distal soft tip 210 and the proximal section 110 of the inner catheter 102, as shown in FIG. 5A.

A flexible tapered element 214 is positioned on the reinforced shaft 212 of the inner catheter 102. The tapered element 214 tapers to a "landing zone" 216. At the landing zone 216, the tapered element 214 has an outer diameter corresponding to the inner diameter at the distal end 112 of the outer catheter 104. As shown in FIGS. 5A-5B, the correspondence of the outer diameter 218 at the widest portion of the tapered element 214 of the inner catheter 102 with the inner diameter 220 at the distal end 112 of the outer catheter 104 provides a seamless transition 220 at the connection between the inner catheter 102 and the outer catheter 104.

As shown in FIG. 5C, the reinforced shaft 114 of the outer catheter 104 has a tapered radiopaque distal tip 224 at the distal end 112 of the outer catheter 104 and reinforcing member 226 which extend along the length of the reinforced shaft 114 of the outer catheter 104. The reinforcing member 226 may be formed with a plurality of elements 228, such as, for example, coils, springs, braids, netting, etc. For example, as shown in FIG. 5C, C-shaped resilient rings 228 are placed in parallel to one another in a spaced apart relationship along the length of the reinforced shaft 114 with an opening 234 between the arms 230, 232 of the rings 228 aligned one with another. It is of importance that the outer catheter or outer member 104 be reinforced to provide structural integrity and maneuverability during the therapeutic procedure. The reinforced structure may be accomplished through the use of a reinforcing type structure such as the C-shaped rings 228 shown formed of a metal construct, a plastic composition or some like material providing reinforcement and sufficient flexibility to allow passage of outer member 104 through a tortuous path during the therapeutic procedure.

Shown in FIG. 5D is a cross-section of the reinforced shaft 114, showing the spring 232 with the arms 228 and 230 forming a space 234 therebetween. In FIG. 5D, the tear cord 196 is shown to extend along the outer catheter groove 154 which coincides with aligned openings 234 of the springs 232 of the reinforced shaft 114.

The reinforced shaft 114 is encapsulated in an elastic plastic sheath 240. The tear wire (cord) 196 extends in the encapsulation 240 along the entire length of the reinforced shaft 114 of the outer catheter 104. When the tear away wire tab 174 is lifted from the outer member tab 120, the tear wire 196 cuts the encapsulating sheath 240, and the reinforced shaft 114 can be split along its tear seam 152.

Referring to FIGS. 6, 7A-7C, 8A-8B, 9, 10A-10C, 11A-11D, 12A-12F, 13A-13B, and 14A-14B, an alternative embodiment of the subject system 200 is shown with a two-sided peel-away design and splittable integrated hemostasis valve.

The two-sided peel-away implementation of the subject system 200 includes an inner member (catheter) 302, an outer member (catheter) 304, an outer member (catheter) peel-away hub 306, and an inner member (catheter) snap-hub 308. The subject inner catheter 302 has a distal section 310, a proximal section 312 (as best shown in FIG. 10B), and an inner catheter shaft 314 extending between the distal section 310 and proximal section 312 of the inner catheter 302. The inner catheter snap hub 308 is positioned at the proximal section 312 of the inner catheter 302.

The inner catheter 302 as shown in FIGS. 6, 7A, 10A-10B, and 11A-11B, is similar to the structure of the inner catheter 102 of the one-sided tear-away implementation of the subject system.

The outer catheter 306 as well as the outer catheter two-sided peel-away hub 324 and the hemostasis valve 326 (as shown in FIGS. 10B-10C) have a design distinct from that of the one-sided tear-away implementation of the subject system.

The outer member (catheter) 306 includes a distal end 316, a proximal end 318, and an outer catheter shaft 320 extending between the distal end 316 and proximal end 318 of the outer catheter 304.

The outer catheter hub 324 positioned at the proximal end 318 of the outer catheter 304 is designed with a quasi-cylindrical body 330 formed by hub walls 332 which have two tear seams 334 and 336 formed through the hub walls 332 of the body 330 of the outer catheter hub 324 spaced angularly about 180° from one another (although angular spacing between the tear seams 334, 336 may be contemplated in the present design).

Figure 9:
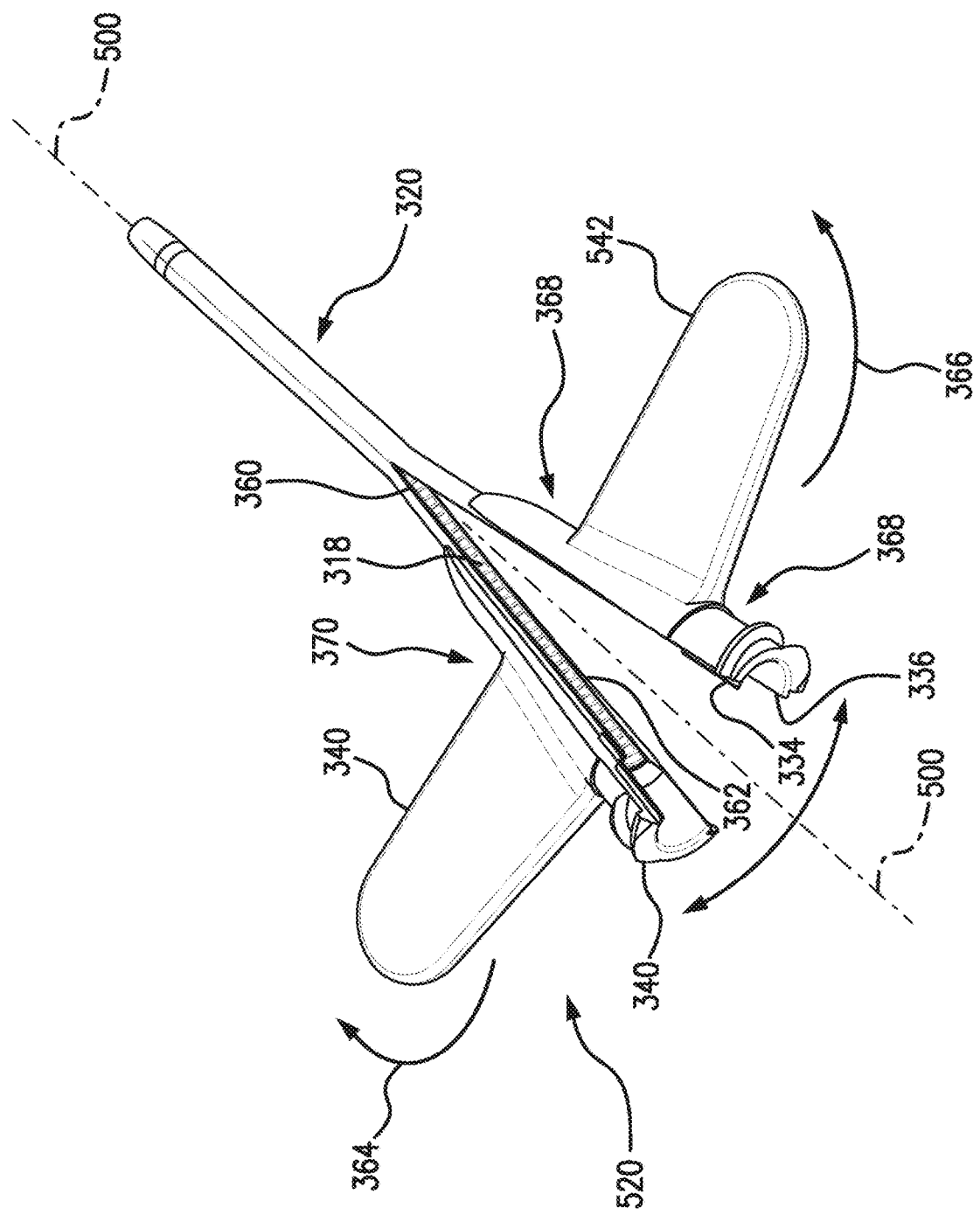
FIG. 9 details the split outer member hub of the two-sided peel-away implementation of the subject system.
Figure 13A:
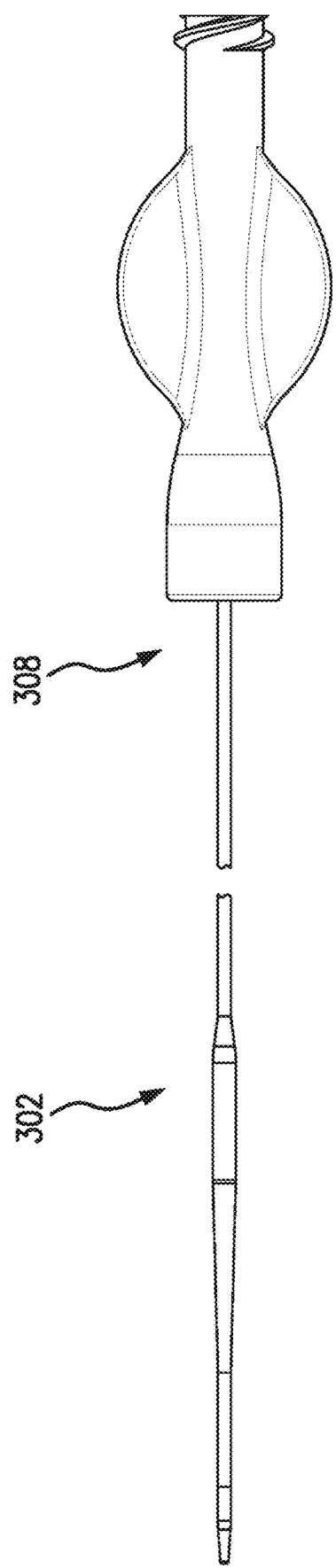
FIGS. 13A-13B show a snap-fit hub version of the inner member, with FIG. 13A showing the inner member coupled to the proximal female Luer lock of the inner member, and FIG. 13B showing a cross-section of the proximal female Luer lock of the inner member.
Figure 13B:
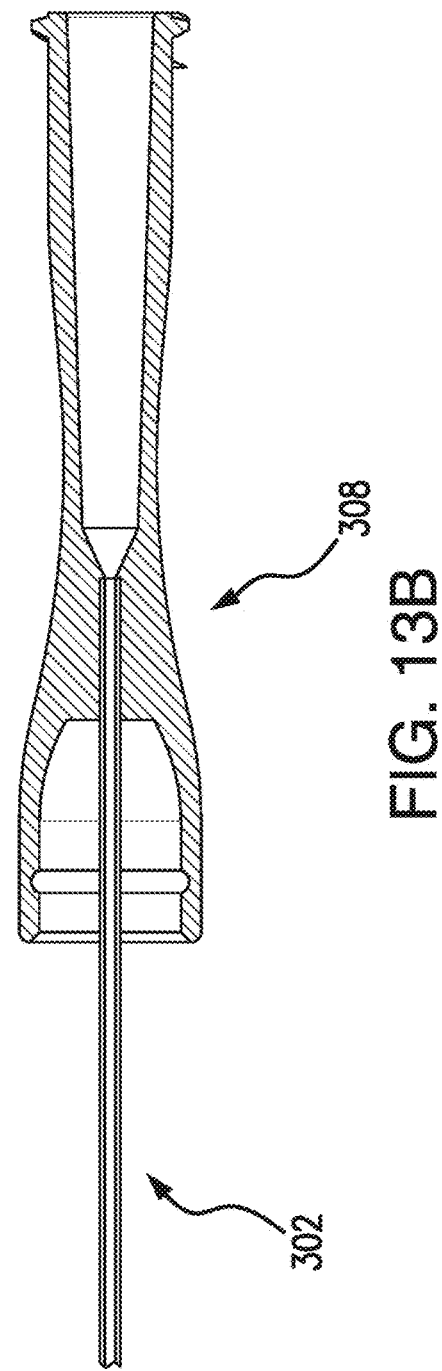

As best shown in FIGS. 7B, 8A-8B, and 9, the outer catheter hub 324 can be split in two symmetrical parts along the tear seams 334 and 336. Specifically, as shown in FIGS. 7B and 9, a Luer lock 340 positioned at the proximal end 342 of the body 330 of the outer catheter hub 324 along with the entire body 330 of the outer catheter hub 324, are splittable structures.

Returning to FIG. 6, the outer catheter hub 324 has wing members 344, 346. At least one side port stopcock 348 is coupled through the side port flexible tubing 350 to the proximal end 318 of the outer catheter 304 (as best shown in FIGS. 10A-10C), similar to the arrangement presented in FIGS. 2, 4A-4B, and 4D. The side port stopcock 348 has multiple ports which serve to connect to fluid removing and supplying systems as necessary for the surgical procedure.

Referring to FIGS. 6, 7A-7C, 8A-8B, 9, 10A-10C, 11A-11C, 12A-12F, 13A-13B, and 14A-14B, in the two-sided peel away implementation of the subject system 200, the outer catheter 304 is splittable in halves. For this, the outer catheter 304 is configured with its outer catheter shaft 320 having a pair of grooves (also referred to herein as tear seams) 360, 362 which extend between the proximal end 318 and distal end 316 of the outer catheter 304. The proximal end 318 of the outer catheter 304 is received within the outer catheter hub 324. When, as required by a surgical procedure, the outer catheter 304 is to be removed from the vasculature structure, the wings 344 and 346 of the outer catheter hub 324 are displaced by a surgeon in the opposite directions 364, 366 (as best shown in FIG. 9). As a result, the outer catheter hub 324 is separated in two halves along the grooves 334 and 336 and the outer catheter's shaft 320 is separated into halves along the outer catheter tear seams 360 and 362, respectively.

The outer catheter hub 324, as best shown in FIGS. 8A-8B, may be composed of two molded portions 368, 370, having similar design and symmetrical with respect to the axis 372 and the axis 374. In order to form the outer catheter half 324, the molded portions 368 and 370 are brought together with the distance between their respective edges 380, and 382, as well as between edges 384 and 386 (shown in FIG. 8A) forming a spaced apart relationship between the edges 380 and 382 at one side of the hub 324 and the space between the edges 384 and 386 at another side of the hub 324. This forms the outer catheter groove 360 (between the edges 384, 386) and the groove 362 (between the edge 380 and the edge 382). The molded portions 368 and 370 when brought together (with the tear seams 360 and 362) are further encapsulated into a flexible envelope 390 (best shown in FIG. 11D) which forms a stable flexible encapsulation for the outer catheter structure.

Referring to FIGS. 11A-11D, representing a distal portion of the subject system, it is seen that the distal portion of the inner catheter 302 has a tapered radiopaque distal tip 394 which is attached to the coil and/or braid reinforced shaft 314 and a tapered element 396 which extends a predetermined and selectable length of the inner catheter shaft 314. The tapered element 396 has a first portion 398 with the diameter increasing from the outer diameter 402 of the inner catheter reinforced shaft 314 to the diameter 404 corresponding substantially to the inner diameter 406 at the distal end 316 of the outer catheter 304.

The diameter 404 is substantially constant along the "landing zone" 400 until the end 408 of the landing zone 400. From the landing zone 400, the tapered element 396 tapers down to the end of the tapered element 396 and returns to the inner diameter corresponding to the outer diameter of the coil reinforced shaft 314 of the inner catheter 302.

Referring to FIG. 11C, the outer catheter 304 is configured with a tapered radiopaque distal tip 412, and the outer catheter's reinforced shaft 320. As shown in FIG. 11C, the reinforced shaft 320 of the outer catheter 304 is built with the outer catheter tear seams 360, 362, extending longitudinally at each side of the shaft outer catheter shaft 320 between the distal end 316 and proximal end 318 thereof (shown in FIGS. 9, 10B and 10C).

The reinforced shaft 320 of the outer catheter 304 is fabricated with the reinforcing system 414 (detailed in further paragraphs) enveloped in the flexible plastic encapsulation layer 390.

The reinforcing system 414 of the two-sided peel-away implementation of the subject system 300 may be, for example, configured as shown in FIGS. 12A-12F. For example, as shown in FIG. 12A-12B, the reinforcing system 414 may be configured as ribs 416 connected to spines 418 and 420 on both sides of the ribs and positioned symmetrically along the length of the outer catheter reinforced shaft 320. The ribs 416 as shown in FIG. 11B extend in a substantially semi-circular (arcuate) configuration in a spaced apart relationship from one another and connected at opposing ends to a respective spine 418 or 420. When in a connected configuration, the spines 418, 420 of both halves of the reinforcing semi-sections 415 are spaced apart to allow formation of the respective groove (tear seam) 360, 362 (also shown in FIG. 11D) of the outer catheter shaft 320. As was the case of the embodiment shown in FIGS. 5A-5C, It is of importance that the outer catheter or outer member 304 be reinforced to provide combined structural integrity and maneuverability during the therapeutic procedure. The reinforced structure may be accomplished through the use of a reinforcing type structure such as the arcuately configured ribs 416, 424, and 432 shown in FIGS. 12A-12B, 12C-12D, and 12E-12F respectively. Ribs 416, 424 and 432 may be formed of a metal construct, a plastic composition or some like material providing reinforcement and sufficient flexibility to allow passage of outer member 304 through a tortuous path encountered in the patient's vessel during the therapeutic procedure. The reinforced structure may be defined by differing contours as provided in FIGS. 12A-12F, or other like arcuate contours. In this embodiment, the spines 418 and 420, 426, as well as 438 and 440 are positioned in substantial alignment with respective tear seams 360 and 362 to provide structural integrity to the seams 360 and 362 for negating pre-mature tearing or ripping of the seams 360 and 362. It is to be understood that the reinforcing structure can be configured in the form of braids, or netting with the overall concept of providing structural integrity while simultaneously allowing enhanced maneuverability during the therapeutic procedure.

In another implementation, shown in FIGS. 12C, 12D, the reinforcing semi-sections 422 include ribs 424 connected to a single spine 426 by one end of each rib 424. In the implementation shown in FIGS. 11C-11D, each rib 424 is a curved (arcuate) structure with one end connected to the spine 426 and another end 428 being disconnected. In this configuration, when forming a reinforced shaft 320 of the outer catheter 304, the spines 426 of both reinforcing semi-section 422 are positioned close to one another with the space therebetween allowing the formation of the tear seam 360. Another tear seam 362 is formed by the ends 428 of the ribs 424 which are spaced one from another to allow the formation of the tear seam 362.

In a further implementation shown in FIG. 12E-12F, each reinforcing semi-section 430 is configured with ribs 432 connected one to another at both sides in an alternating manner. Specifically, as shown in FIG. 12F, each rib 432 has opposite ends 434 and 436. The ends 434 are connected by connecting spine elements 438 in an alternating fashion, while the ends 436 of the ribs 432 are connected in the alternating manner by the connecting elements 440. When two reinforcing semi-sections 430 shown in FIGS. 12E-12F are brought together to form the reinforced outer catheter shaft 320, the connecting elements 438 are positioned in parallel relationship to the connecting elements 438 of another reinforcing semi-section 430 with the distance therebetween permitting an outer catheter groove 360 to be formed. Similarly, the connecting elements 440 of one of the reinforcing semi-sections 430 is brought into parallel relationship with corresponding connecting elements 440 of another (complementary) reinforcing semi-section 430 with a small distance therebetween to allow formation of the outer catheter tear seam 362 therebetween.

The embodiment of the outer catheter shaft's ring reinforcement configurations presented in FIG. 12A-12F are exemplary implementations, however other reinforcement structures which allow formation of two (or more) tear seams in the outer catheter shaft 320 are considered applicable in the present structure.

When the inner catheter 302 is inserted into the outer catheter 304 as shown in FIG. 10B, in a connected manner, the inner catheter's tapered element 396 is inserted within the tapered tip 412 of the outer catheter 304, the inner diameter 406 corresponds to the outer diameter 404 of the landing zone 400 of the tapered element 396 on the inner catheter 302. Such arrangement with the diameter of the tapered element 396 at the landing zone 400 of the inner catheter 392 corresponding to the inner diameter 406 of the tapered tip 412 of the outer catheter 304 provides a seamless transition 450 between the inner catheter 302 and the outer catheter 304 for optimized pushability of the structure and for reduced traumatization to the vascular structure during the surgical procedure.

The outer catheter hub and the inner catheter hub form together an interconnection mechanism which is controlled by a surgeon to attain either an "engaged" or "disengaged" mode of operation.

Figure 4A:
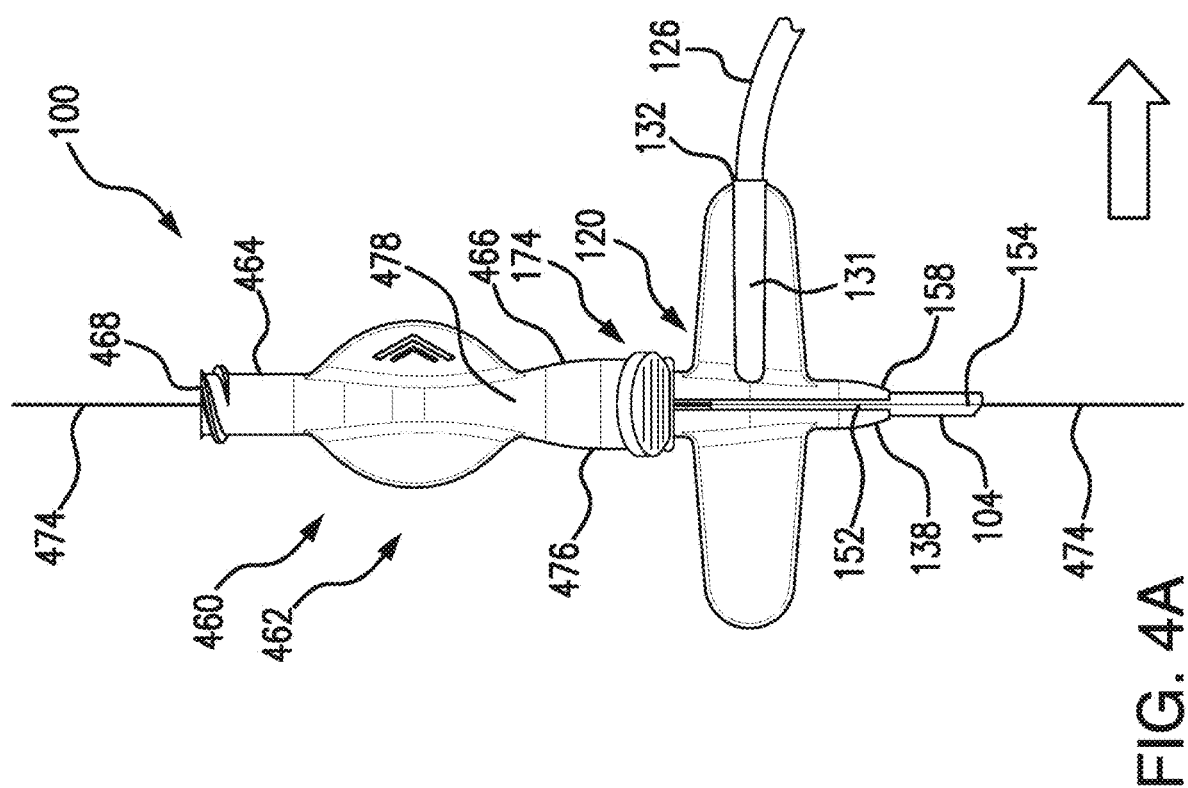
Figure 6:
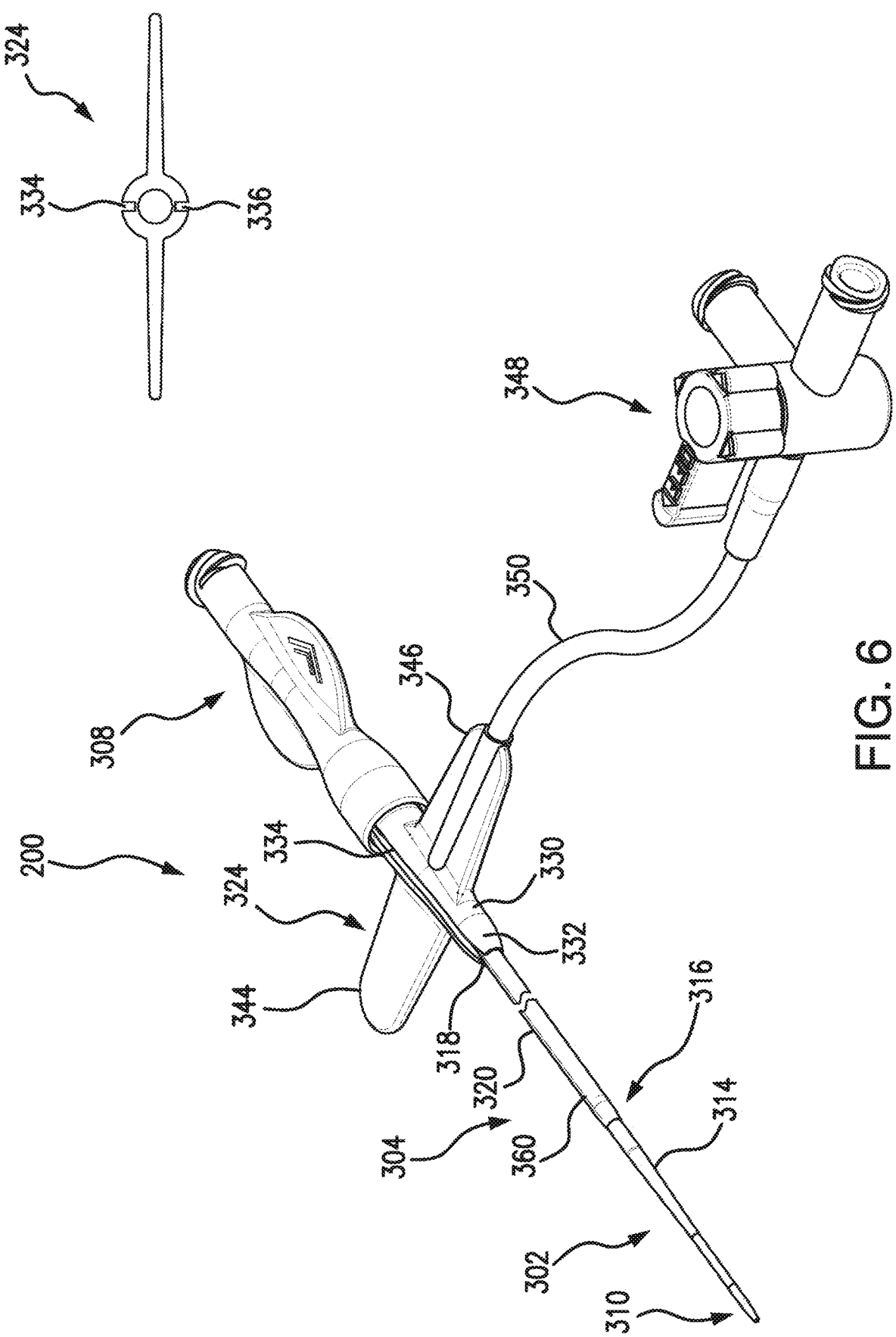
FIG. 6 depicts the subject system in a two-sided peel-away implementation.

Referring now to FIGS. 2, 4A-4B, 6, 7A, 7C, 10A-10B, the proximal portion of the inner catheter is removably coupled to the proximal section of the outer catheter through the inner catheter hub 460 and the outer catheter hub 120. For example, as shown in FIGS. 2 and 4A-4B, the inner catheter hub 460 has an elongated body 462 which has a proximal end 464 and a distal end 466. The proximal end 464 of the inner catheter hub 460 includes a port 468 (for the guide wire 474) which forms an entrance into an internal channel 470 of the inner catheter hub 460 which extends between the proximal end 464 and the distal end 466 of the hub and terminates in, and is connected to the proximal end (section) 110 of the inner catheter 102.

In operation, the port 468, internal channel 470 and the internal lumen of the inner catheter 102 serve as a passageway for the guidewire 474.

At the distal end 466, the elongated body 462 of the inner catheter hub 460 has a quasi-cylindrical portion or section 476, the walls 478 of which define an internal tunnel 480 with a cylindrical indentation 482 extending annularly around the inner surface of the walls 478 of the internal tunnel 480.

As shown in FIGS. 4B and 4D, circular protrusions 484 are formed at the outer surface 486 of the proximal portion 190 of the outer catheter hub 120. In this implementation, the inner catheter hub 460 is a female type structure, while the outer catheter hub 120 forms a male type structure. When the female inner catheter hub 460 receives in its distal portion 476 the proximal portion 190 of the outer catheter hub 120, the circular indentation 482 of the inner catheter hub 460 receives and matches with the circular protrusion 484 on the outer catheter hub 120 to provide a secure snap-fit connection of the hubs 120 and 460 to each other. This results in engagement of the inner catheter 102 to the outer catheter 104 in order that a surgeon can manipulate both catheters 102, 104 together in the engaged mode of operation. When the inner catheter 102 and outer catheter 104 are to be separated one from another, the inner catheter hub 460 and the outer catheter hub 120 are displaced one from another, so that the system can be operated in its disengaged mode of operation, as required by the particular surgical procedure.

The tear-away wire tab 174, when placed on the proximal portion 190 of the outer catheter hub 120, results in a locked mode of operation which prevents the hub 120, the hemostasis valve 122, and the outer catheter 104 from being split and torn-away.

As shown in FIGS. 2, 4A-4B, in operation, the inner catheter snap-hub 460 is snapped onto the proximal section 190 of the outer catheter hub 120, and the tear-away wire tab 174 locks on the proximal section 190 of the outer catheter hub 120. The outer catheter hub 120, the outer catheter 104, as well as the valve 122 remain in close (locked) configuration along with the inner catheter 102 locked within the outer catheter 104. In this configuration, the distal section 106 of the inner catheter 102 extends from the distal portion 112 of the outer catheter 104, so that the surgeon can advance the system 100 into the vasculature structure in the locked configuration along the guidewire 474 positioned in the vasculature. The inner catheter 102 slides along the guidewire 474 as required by the surgical procedure.

When delivered with the tapered distal soft tip 210 (positioned at the distal section 106 of the inner catheter 102) to the target site, the inner catheter hub 460 is disconnected (unsnapped) from the outer catheter hub 120 and may be removed from the outer catheter hub 120 by pulling the inner catheter hub 460 away from the outer catheter hub 120. Prior to removal of the inner catheter 12 from the vasculature, the outer catheter 104 may distally advance along the inner catheter 102 further towards (and/or beyond) the target site inside the blood vessel. FIG. 4D shows the cross-section of the outer catheter hub 120 with the inner catheter 102 removed therefrom.

When the inner catheter 102 is removed from the outer catheter 104, a pacemaker lead 500 (or other therapeutic structure) can be delivered through the outer catheter 104 to the target site. As shown in FIGS. 3 and 4D, the pacemaker lead 500 enters the internal channel 164 of the valve 122 and at the proximal end 140 of the hub 120 is delivered to the target site along the internal lumen 502 of the outer catheter 104. Subsequent to the delivery of the pacemaker lead (or other therapeutic catheter) 500 to the target site, the outer catheter 104 along with the hemostasis valve 122 can be easily removed from within the vasculature structure in an easy and rapid manner without causing traumatization to the tissue of the vasculature structure. For this, the tear-away wire tab 174 is removed from the proximal portion 190 of the outer catheter hub 120. When lifted from the outer catheter hub 120, the tear-away wire tab 174 pulls the tear cord 196 which results in cutting through the encapsulation 230 by the tear cord 196. Subsequently, the wings 128 and 130 of the hub 120 are angularly displaced along the directions 202, 204 so that the outer catheter splits along the groove 152. The valve 122 is also split along the groove 170, and the outer shaft 114 of the outer catheter 104 splits along its tear seam 154. This arrangement allows an easy removal of the valve 122, outer catheter hub 120, and the outer catheter 104 from the pacemaker lead 500 and from within the vasculature structure.

In the two-sided peel-away implementation of the subject system 200, as shown in FIGS. 6, 10A-10B, and 13A-13B, the inner catheter snap-hub 308 provides a snap-fit connection with the outer catheter hub 324. The implementation of the snap-hub 308, shown in FIGS. 6,10A-10B, and 13A-13B, is similar to the design of the snap-inner catheter hub 460 presented in FIGS. 2 and 4A-4B. However in this implementation, the outer catheter hub 324 is split along two grooves 334 and 336.

In a further alternative embodiment, shown in FIGS. 7A, 7C, and 14A-14B, the inner catheter hub 510 has a hub body 512 with the proximal section 514 and a distal section 516 which forms a male Luer lock connection (lock) with a rotating threaded collar 518. The outer catheter hub 520 in the implementation shown in FIGS. 7A-7C has a body 522 with a distal portion 524 and a proximal portion 526 configured as a female type Luer lock with exterior threads 528.

As shown in FIG. 7C, the male Luer lock (distal section) 516 of the inner catheter hub 510 is received in and couples with the proximal portion 526 (female Luer lock) of the outer catheter hub 520. The rotating threaded collar 518 connects the outer catheter hub 520 and the inner catheter hub 510 by its internal threaded configuration 530 with the exterior threads 528 of the Luer lock 526 of the outer catheter hub 520. When the rotating threaded collar 518 connects the inner catheter hub 510 and the outer catheter hub 520 as shown in FIG. 7A, 7C, the inner catheter 302 is locked within the outer catheter 304, and during this stage of procedure, the surgeon can manipulate both inner catheter 302 and outer catheter 304 in a locked (engaged) configuration with the inner catheter advancing along the guidewire 474.

As shown in FIGS. 7A-7C, the proximal section 514 of the inner catheter hub 510 is a proximal female Luer lock with an internal channel 532 terminating in the proximal port 534 which is the guidewire port. The guidewire 474 extends through the channel 532 and the internal lumen of the inner catheter 302. In order to connect the outer catheter hub 520 and the inner catheter hub 510 as shown in FIGS. 7A and 7C, the female type distal portion 524 of the outer catheter hub 520 receives the male type distal section 516 on the Luer lock 526 of the inner catheter hub 510.

When the inner catheter 302 is decoupled from the outer catheter 304, the rotating threaded collar 518 disengages from the external threads 528 on the Luer lock 526 of the outer catheter hub 520, and the distal section 516 of the inner catheter hub 510 may be displaced from the outer catheter hub 520. In this configuration, the inner catheter 302 may be removed from the outer catheter 304 as shown in FIG. 10C. When the inner catheter 302 is pulled out by the inner catheter hub 510 from the outer catheter 304, the outer catheter 304 remains attached to the outer catheter hub 520 with the valve 326 integrated in the outer catheter hub 520 as shown in FIG. 10C.

Subsequent to removal of the inner catheter hub 510 and the inner catheter 302, a pacemaker lead (or other therapeutic catheter) 500 can be inserted to the target site through the outer catheter 104. When the pacemaker lead 500 is deployed in position (i.e., at and secured at the target site), the outer catheter 304 may be removed rapidly in a trauma-free manner from the vasculature structure. As shown in FIG. 9, the wings 540 and 542 of the outer catheter hub 520 are separated in opposite directions 364, 366, as shown in FIG. 9. This action results in the separation of the outer catheter hub 520 into two symmetrical, similarly configured portions of the outer catheter hub 520, with the splitting of the valve 326 in two similar identical halves (as shown in FIG. 10D), and separation of the outer catheter shaft 320 along the tear seams 360 and 362 into symmetrical molded portions 368, 370. Being separated in two parts 368, 370, the outer catheter is simply peeled from the pacemaker lead 500 and is removed from the vasculature structure. The pacemaker lead (or the other therapeutic structure) remains in position in the vasculature structure.

Referring to FIGS. 15A-15B, alternative distal tip variations are contemplated in the subject system, including the 90° angled inner catheter tip 394', as presented in FIG. 15A, and the 120° angled inner catheter tip 394", as shown in FIG. 15B. Although two angled configurations are presented in FIGS. 15A-15B, other angled configurations for the inner catheter tip 394 are possible and contemplated within the scope of the present system. The angled configurations for the inner catheter tip 394 provide improved maneuverability of the inner catheter 302 while being slid along the guidewire.

Figure 16A:
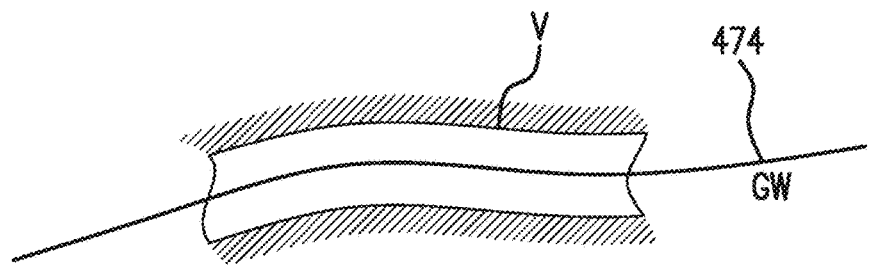
FIGS. 16A-16E depict schematically the subject surgical process for insertion of a pacemaker lead into a blood vessel using the subject system.

In the surgical procedure, as shown in FIG. 16A, the guidewire 474 is inserted into the vasculature structure V of interest and extends inside the vascular structure.

Figure 16B:
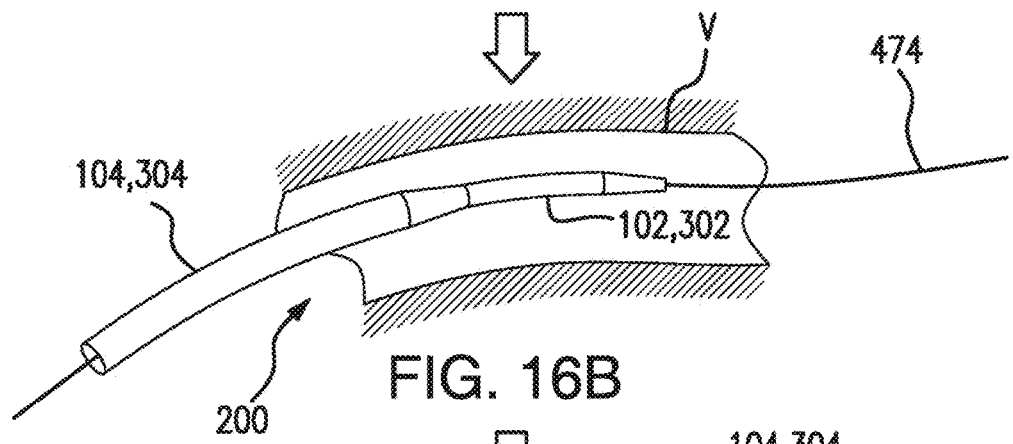

Subsequently, as shown in FIG. 16B, the inner catheter 102, 302 and outer catheter 104, 304 are locked one to the other by locking the inner catheter hub 460, 510 to the outer catheter hub 120, 520. In a one-side tear-away implementation, shown in FIGS. 2-5, the tear-away wire tab 174 is locked onto the outer catheter hub 104 (FIGS. 2, 4A-4B). The locked structure with the inner catheter locked inside the outer catheter is shown in FIG. 16B.

Figure 16C:
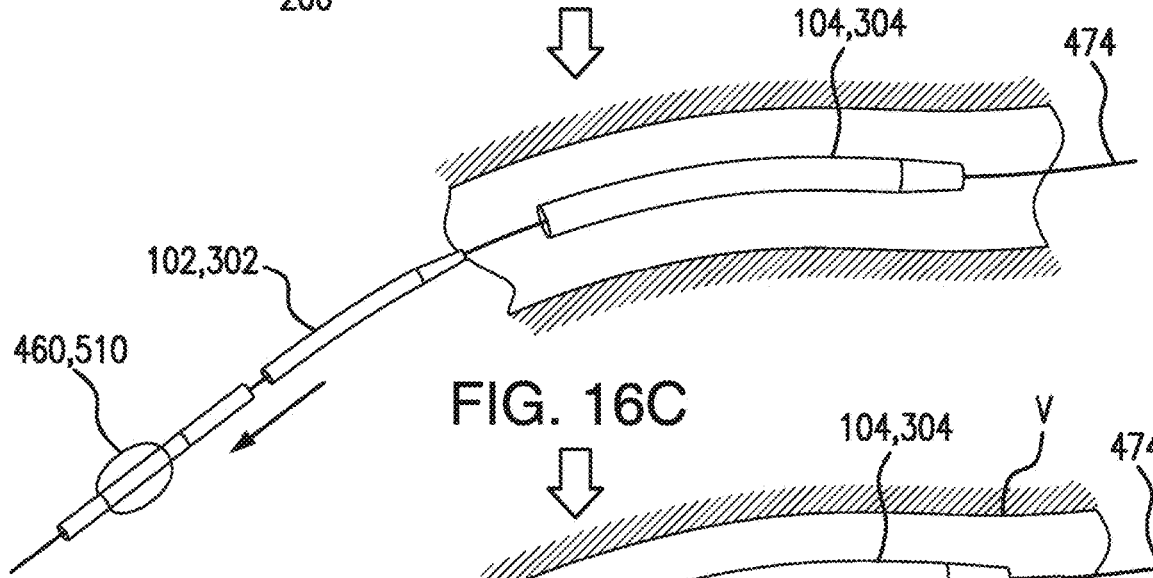

When in place, the inner catheter 102, 302 is unlocked from the outer catheter 104, 304 by unlocking the inner catheter hub from the outer catheter hub, and the outer catheter, if needed, can slide further along the inner catheter towards (and/or beyond) the target site. Subsequently, as shown in FIG. 16C, by pulling the inner catheter hub 460, 510 in the direction away from the vasculature or vessel V, the inner catheter 102, 502 is removed from the outer catheter 104, 204, which remains in the blood vessel V.

Figure 16D:
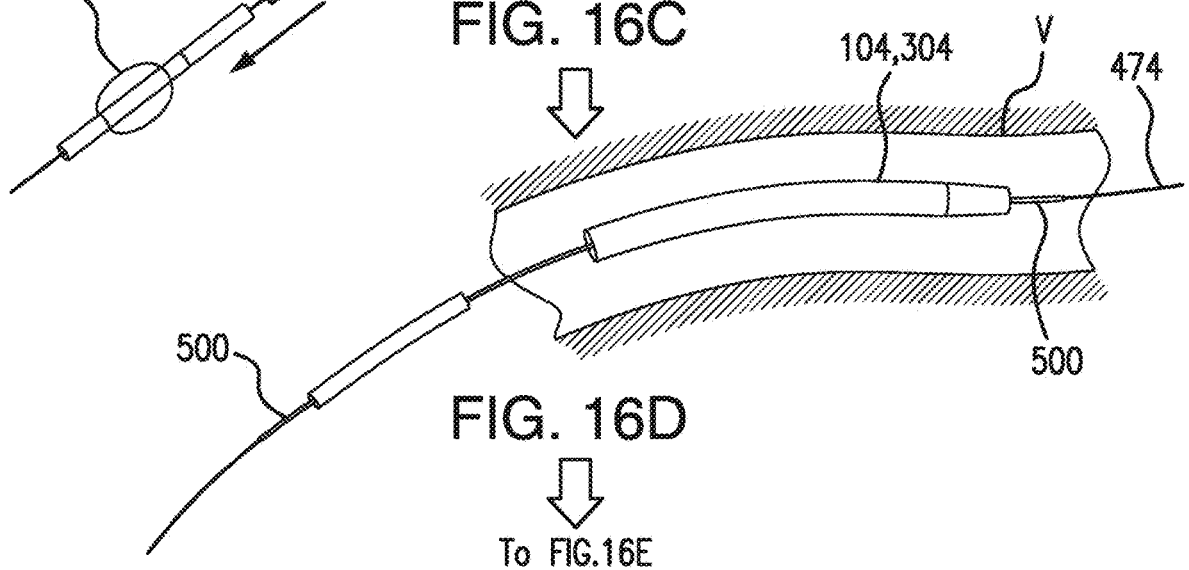
Figure 16E:
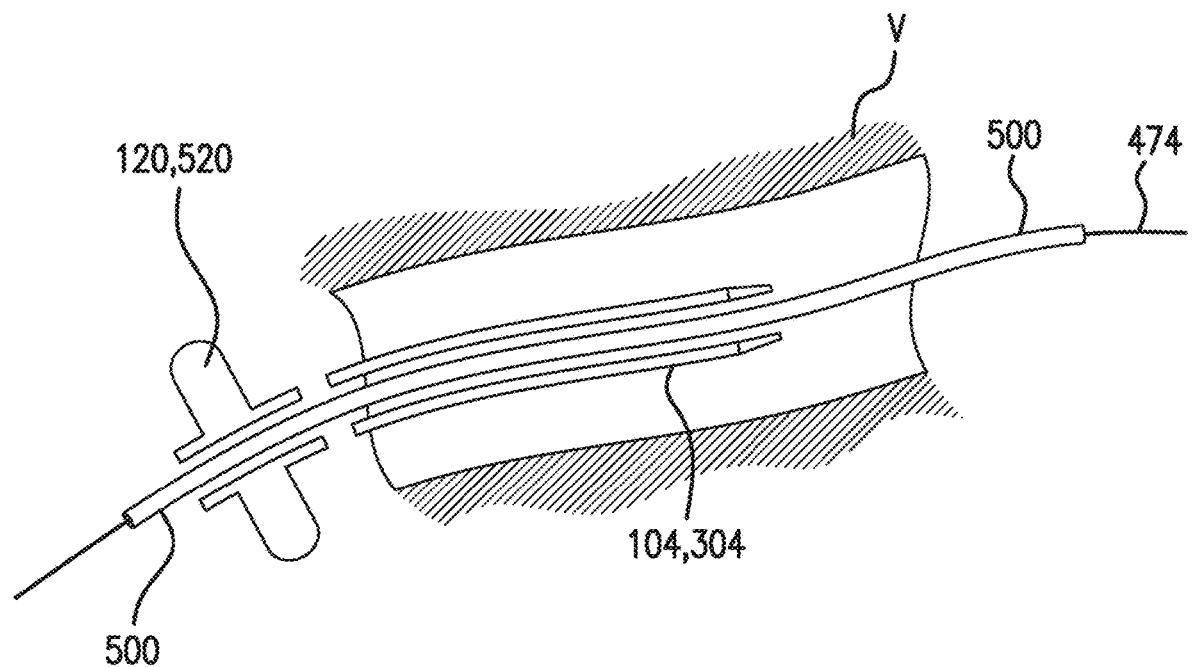

Subsequently, as shown in FIG. 16D, a pacemaker lead (or other therapeutic catheter 500) may be inserted into the blood vessel V along the guide wire 474 through the outer catheter (and specifically through the hemostasis valve, the outer catheter hub, and through the internal lumen of the outer catheter) to the area of interest within the vasculature.

When the pacemaker lead 500 is installed in the vasculature V at the site of interest, the outer catheter 104, 304 may be removed from the vasculature structure V in an easy, rapid, and safe manner by slipping the outer catheter hub 120, 520 along with the hemostatic valve, and the outer catheter shaft (as shown in FIGS. 3, 4D-4E, 5C-5D, 8A-8B, 9, 10C-10D, 11C-11D) at one longitudinal tear groove (seam or two longitudinal grooves/seams) provided for this purpose. The hemostasis valve integrated in the outer catheter hub is split at one or two longitudinal grooves, similar in manner to the outer catheter hub, and the outer catheter. When such separates, the outer catheter is removed from the vasculature in an efficient, safe, and substantially trauma-free manner.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. An intravascular delivery system configured for efficient delivery of a therapeutic catheter to a target site in a blood vessel of interest, comprising:

a splittable outer member configured by a flexible substantially cylindrically contoured wall forming an elongated outer delivery sheath, said outer delivery sheath defining a sheath lumen having a proximal end, a distal end, and an outer member shaft extending between said proximal end and said distal end, wherein said outer member shaft is configured with a tapered outer tip at said distal end of said sheath lumen and at least one tear seam extending longitudinally along said cylindrically contoured wall of said splittable outer member between said proximal and distal ends of said sheath lumen, wherein said splittable outer member assumes a closed configuration when said at least one tear seam is intact and a split configuration, when said at least one tear seam is opened, wherein said outer member shaft includes a reinforcement structure extending along a length of said outer member shaft between said proximal and distal ends of said sheath lumen thereof, a flexible encapsulating sheath enveloping said outer member shaft, and a tear wire encapsulated in said flexible encapsulating sheath in alignment with said at least one tear seam of said outer member shaft;

an inner member having an elongated body formed by an inner member wall, said inner member wall defining an internal channel extending along the longitudinal axis of said inner member, wherein said inner member is removably received in and extends internally along said sheath lumen of said splittable outer member in a controllable relationship with said outer delivery sheath, said inner member having a proximal end and a tapered distal tip displaceable along a guide wire beyond said distal end of said outer delivery sheath; and an interconnection mechanism disposed in an operative coupling with said inner member and said splittable outer member and controllably actuated to operate said intravascular delivery system intermittently in an engaged and disengaged mode of operation;

wherein, in said engaged mode of operation, said inner member and splittable outer member of said intravascular delivery system are engaged for a controllable common displacement along the guide wire;

wherein, in said disengaged mode of operation, said inner and outer members are disengaged for displacement of said inner member and said splittable outer member relative one another;

wherein, in said disengaged mode of operation, said splittable outer member is split along said at least one tear seam thereof for removal from said blood vessel of interest, an inner member hub secured to said proximal end of said inner member;

a splittable outer member hub secured to said proximal end of said sheath lumen of said splittable outer member, said splittable outer member hub having an elongated body configured by an outer member hub wall, a pair of wing members attached to said elongated body and extending in opposite directions therefrom, wherein said splittable outer member hub wall is formed with at least one tear groove extending longitudinally along said splittable outer member hub wall of said elongated body of said splittable outer member hub between proximal and distal ends of said elongated body of said splittable outer member hub, said at least one tear groove of said splittable outer member hub being aligned with said at least one tear seam of said outer delivery sheath of said splittable outer member, wherein said splittable outer member hub assumes a closed configuration when said at least one tear groove is closed, and a split configuration when said at least one tear groove is opened;

wherein said interconnection mechanism is configured by an interrelation between said inner member hub and said splittable outer member hub to prevent or permit a displacement of said inner member relative to said outer member; and wherein, in said disengaged mode of operation, said outer member hub is split along said at least one tear groove thereof, wherein, in said disengaged mode of operation, said splittable outer member is split along said at least one tear seam thereof for removal from said blood vessel of interest, wherein said splittable outer member hub comprise external threads proximal to the pair of wing members, wherein the at least one tear groove extending longitudinally along said splittable outer member hub wall of said elongated body of said splittable outer member hub extends through the external threads, wherein said inner member hub has an inner member hub elongated body configured with a proximal portion a distal portion, wherein distal portion configured to be at least partially received within said splittable outer member hub, said system further comprising a rotating threaded collar having internal threads and positioned externally on said distal portion of said elongated body of said inner member hub, and wherein said external threads of said splittable outer member hub cooperating with a first portion of said internal threads of said rotating threaded collar.

2. The intravascular delivery system of claim 1, further including a tear-away wire tab member configured with a tab and a C-shaped spring wire member attached to said tab and configured to be removably snapped on the splittable outer member hub at a proximal end of an elongated body of said splittable outer member hub to maintain said elongated body of said splittable outer member hub in said closed configuration, wherein said tear wire has a proximal end attached to said tear-away wire tab member, wherein in said closed configuration of said splittable outer member and splittable outer member hub, said tear wire extends within said at least one tear groove of said splittable outer member hub and said at least one tear seam of said splittable outer member, and wherein, said splittable outer member and said splittable outer member hub are converted from said closed configuration in said split configuration by disengaging said tear-away wire tab member from said splittable outer member hub, resulting in opening of said at least one tear groove of said splittable outer member hub and ripping said encapsulating sheath of said splittable outer member along said at least one tear seam.

3. The intravascular delivery system of claim 2, wherein said elongated body of said splittable outer member hub includes an internal channel defined by said outer member hub wall and a proximal portion housing a splittable hemostasis valve integrated therein, said splittable hemostasis valve being configured with a cylindrical body having a valve wall and a longitudinal channel formed by said wall in communication with said internal channel of said splittable outer member hub, said valve wall of the cylindrical body of said splittable hemostasis valve being formed with at least one valve groove extending along said wall through the thickness thereof, said at least one valve groove extending along and in alignment with said at least one tear groove of said splittable outer member hub, wherein said hemostasis valve assumes a split configuration when said splittable outer member hub is split.

4. The intravascular delivery system of claim 3, further including a side port stopcock sub-system fluidly coupled to said proximal end of said splittable outer member installed in said splittable outer member hub through a side port flexible tubing coupled to at least one wing member of the pair of wing members of said splittable outer member hub.

5. The intravascular delivery system of claim 3, wherein the valve wall of said cylindrical body of said splittable hemostasis valve is configured with at least two parallel valve grooves spaced apart along a perimeter of said valve wall of said cylindrical body of said splittable hemostasis valve.

6. The intravascular delivery system of claim 1, wherein said outer member shaft is configured with at least a pair of parallel tear seams spaced apart along a perimeter of said splittable outer member, and wherein said outer member hub wall of said elongated body of said splittable outer member hub is configured with at least two parallel tear grooves spaced apart along a perimeter of said outer member hub wall in alignment with said at least two tear seams of said outer member shaft.

7. The intravascular delivery system of claim 1, wherein said inner member hub is configured with a central portion between said distal and proximal portions of said inner member hub elongated body, said distal portion being formed by a quasi-cylindrical wall defining an inner distal cavity having an internal surface, said proximal and central portions of said inner member hub's elongated body having an internal channel extending longitudinally between a proximal port of said inner member hub and said inner distal cavity of said distal portion of said inner member hub, wherein said proximal end of said inner member extends along said inner distal cavity and is secured to said inner channel of said inner member hub.

8. The intravascular delivery system of claim 7, wherein said elongated body of said splittable outer member hub is configured with a proximal portion having proximal portion wall having an outer surface and defining an internal channel having an internal surface, wherein in said engaged mode of operation, said proximal portion of said splittable outer member hub is snuggly received and secured in said inner distal cavity of said distal portion of said inner member hub.

9. The intravascular delivery system of claim 8, further including an annular groove extending annularly at the internal surface of said inner distal cavity of said inner member hub, and an annular protrusion extending at the outer surface of said proximal portion wall of said splittable outer member hub in matching relationship with said annular groove of said inner member hub, said annular protrusion engaging into said annular groove to enhance the coupling between said inner member hub and said splittable outer member hub.

10. The intravascular delivery system of claim 1, wherein said reinforcement structure of said splittable outer member shaft includes a plurality of arcuated ribs, each rib having a first end and a second end, said plurality of arcuated ribs being positioned in a spaced apart relationship with one another along the length of said outer member shaft and connected at least at one of said first and second ends by a spine structure.

11. The intravascular delivery system of claim 10, wherein said first ends of said arcuated ribs are connected by a first spine structure, and said second ends of said arcuated ribs are connected by a second spine structure in an alternating order.

12. The intravascular delivery system of claim 1, wherein said pair of wing members on said splittable outer member hub are displaced in opposite directions angularly or linearly one from another to split said splittable outer member hub and said splittable outer member.

* * * * *